(12) United States Patent
Liesenfelt et al.

(10) Patent No.: US 9,123,450 B2
(45) Date of Patent: Sep. 1, 2015

(54) SINGLE BEAM BACKSCATTER X-RAY SYSTEM

(75) Inventors: Michael Liesenfelt, Knoxville, TN (US); William Talion Edwards, Foristell, MO (US); Daniel Shedlock, Knoxville, TN (US)

(73) Assignee: The Boeing Company, Chicago, IL (US)

( * ) Notice: Subject to any disclaimer, the term of this patent is extended or adjusted under 35 U.S.C. 154(b) by 709 days.

(21) Appl. No.: 13/460,041

(22) Filed: Apr. 30, 2012

(65) Prior Publication Data

US 2013/0287169 A1 Oct. 31, 2013

(51) Int. Cl.
*G01N 23/203* (2006.01)
*G21K 1/04* (2006.01)
*G01N 23/00* (2006.01)
*G21K 5/04* (2006.01)
*G01K 1/02* (2006.01)

(52) U.S. Cl.
CPC .. *G21K 1/04* (2013.01); *G01K 1/02* (2013.01); *G01N 23/005* (2013.01); *G01N 2223/063* (2013.01); *G01N 2223/3301* (2013.01); *G01N 2223/646* (2013.01); *G21K 5/04* (2013.01)

(58) Field of Classification Search
CPC .......... H01J 37/252; G01N 2021/4709; G01N 23/04; G01N 2223/055; G01N 23/203; G01N 2223/646; G01N 2223/063; G01N 23/20066; G21K 1/04; G21K 1/01; G21K 1/02; G21K 1/043; G21K 5/10; G21K 5/04; H05G 1/02; B64F 5/0045; H05H 3/06
USPC ...................... 378/58, 87, 147, 149, 160, 161
See application file for complete search history.

(56) References Cited

U.S. PATENT DOCUMENTS

| | | | | |
|---|---|---|---|---|
| 2,497,755 | A * | 2/1950 | Berggren | 378/150 |
| 4,145,616 | A * | 3/1979 | Tanabe | 378/150 |
| 4,342,914 | A | 8/1982 | Bjorkholm | |
| 4,472,822 | A | 9/1984 | Swift | |
| 5,224,144 | A | 6/1993 | Annis | |
| 5,278,886 | A * | 1/1994 | Kobiki et al. | 378/65 |
| 7,593,506 | B2 | 9/2009 | Cason | |
| 8,033,724 | B2 | 10/2011 | Edwards et al. | |
| 2005/0157844 | A1 * | 7/2005 | Bernardi et al. | 378/57 |

OTHER PUBLICATIONS

Sponder, An Assessment of Comscan, a Compton Backscatter Imaging Camera, for the One-Sided Non-destructive Inspection of Aerospace Components, 1993, Aeronautical Research Labs Melbourne Australia, report No. ARL-TR-34.*

* cited by examiner

*Primary Examiner* — David J Makiya
*Assistant Examiner* — John Corbett
(74) *Attorney, Agent, or Firm* — Yee & Associates, P.C.

(57) ABSTRACT

A method and apparatus for inspecting an object is present. Radiation is emitted from a radiation source. A beam is formed from a portion of the radiation emitted by the radiation source using a collimator. The collimator is connected to the radiation source by a bearing system comprising a first structure associated with the radiation source and a second structure connected to the first structure. The second structure is configured to hold the collimator. The second structure of the bearing system is moved using a movement system such that the second structure rotates in one of a plurality of directions substantially about a center point in the radiation source while the radiation source remains stationary relative to the second structure. Rotation of the second structure substantially about the center point in the radiation source changes a direction in which the beam is directed.

14 Claims, 18 Drawing Sheets

SINGLE BEAM BACKSCATTER X-RAY SYSTEM

BACKGROUND INFORMATION

1. Field

The present disclosure relates generally to inspection systems and, in particular, to backscatter inspection systems. Still more particularly, the present disclosure relates to a method and apparatus for inspecting an object by moving a beam of radiation along the object in a selected pattern and detecting the backscatter formed in response to the beam encountering the object.

2. Background

Some currently available nondestructive inspection systems use radiation to inspect an object. The radiation may take the form of, for example, without limitation, x-rays, gamma rays, neutrons, or some other suitable type of radiation. A backscatter x-ray system is one example of a nondestructive inspection system that uses x-rays to inspect an object.

Some currently available backscatter x-ray systems include an x-ray tube, a collimator, and a detector system. The x-ray tube generates and emits x-rays. The collimator filters these x-rays to form an x-ray beam using the portion of the x-rays that travels parallel to a specified direction. This x-ray beam may be referred to as a pencil x-ray beam in some cases. During inspection of an object, the collimator is positioned such that the x-ray beam is directed toward the object.

When the x-ray beam encounters the object, some or all of the x-rays in the x-ray beam are scattered by the object. These scattered x-rays are referred to as backscatter. The detector system detects some or all of this backscatter. The detected backscatter may be used to generate image data for the object that can be used to form one or more images of the object. For example, the backscatter detected when the x-ray beam is directed at a particular location on the object may be used to generate a value for a pixel in an image that corresponds to that particular location on the object.

The x-ray beam may be moved along the object in a selected pattern such that image data may be generated for different locations on the object. This pattern may be, for example, a raster pattern. In particular, the x-ray beam may be oscillated along the object. Oscillating an x-ray beam includes moving the x-ray beam back and forth in a particular direction. The backscatter x-ray system may be mounted on a moveable platform that moves the backscatter x-ray system such that the x-ray beam may be oscillated in different directions substantially parallel to each other. The image data may then be used to form one or more images of the object. These images may be used to determine whether any inconsistencies are present in the object.

With some currently available backscatter x-ray systems, oscillating an x-ray beam along the object requires moving both the x-ray tube and the collimator at the same time independently of the moveable platform. In other words, moving the x-ray beam from one location on the object to another location on the object requires that both the collimator and the x-ray tube be moved. The number of components needed to move both the x-ray tube and the collimator such that the x-ray beam may be moved along the object in a selected pattern may be greater than desired with these currently available backscatter x-ray systems. Further, the weight and/or complexity of these types of backscatter x-ray systems may be greater than desired.

Therefore, it would be desirable to have a method and apparatus that takes into account at least some of the issues discussed above, as well as other possible issues.

SUMMARY

In one illustrative embodiment, an apparatus comprises a radiation source, a collimator, a bearing system, and a movement system. The radiation source is configured to emit radiation. The collimator is configured to form a beam using a portion of the radiation emitted by the radiation source. The bearing system is configured to connect the collimator to the radiation source. The bearing system comprises a first structure associated with the radiation source and a second structure connected to the first structure. The second structure is configured to hold the collimator. The movement system is configured to move the second structure of the bearing system such that the second structure rotates in one of a plurality of directions substantially about a center point in the radiation source while the radiation source remains stationary relative to the second structure. Rotation of the second structure substantially about the center point changes a direction in which the beam formed by the collimator is directed.

In another illustrative embodiment, a method for inspecting an object is present. Radiation is emitted from a radiation source. A beam is formed from a portion of the radiation emitted by the radiation source using a collimator. The collimator is connected to the radiation source by a bearing system comprising a first structure associated with the radiation source and a second structure connected to the first structure. The second structure is configured to hold the collimator. The second structure of the bearing system is moved using a movement system such that the second structure rotates in one of a plurality of directions substantially about a center point in the radiation source while the radiation source remains stationary relative to the second structure. Rotation of the second structure substantially about the center point in the radiation source changes a direction in which the beam is directed.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the different illustrative embodiments recognize and take into account that some currently available backscatter x-ray systems weigh more than desired. This increased weight may prevent these backscatter x-ray systems from being used in certain locations or used to inspect certain types of objects.

Further, the different illustrative embodiments recognize and take into account that the increased weight of these backscatter x-ray systems may be attributed to the shielding materials used in these backscatter x-ray systems. Shielding materials are materials used to provide protection from radiation, such as, for example, x-rays. These shielding materials may absorb and/or scatter x-rays such that the x-rays are not allowed to pass through the shielding materials.

With some currently available backscatter x-ray systems, shielding material may be required to fully wrap around the x-ray tube. The different illustrative embodiments recognize and take into account that by reducing the amount of shielding material used around an x-ray tube, the weight of a backscatter x-ray system may be reduced.

Additionally, the different illustrative embodiments recognize and take into account that an x-ray source that is moving relative to the moveable platform on which the backscatter x-ray system is mounted during operation of the x-ray source may have a shorter life expectancy than an x-ray source that remains stationary relative to the moveable platform. In particular, high frequency motion and oscillation of the x-ray source may reduce the life expectancy of the x-ray source.

Thus, the illustrative embodiments provide a method and apparatus for inspecting an object. In one illustrative embodiment, an apparatus comprises a radiation source, a collimator, a bearing system, and a movement system. The radiation source is configured to emit radiation. The collimator is configured to form a beam using a portion of the radiation emitted by the radiation source. The bearing system is configured to connect the collimator to the radiation source. The bearing system comprises a first structure associated with the radiation source and a second structure connected to the first structure. The second structure is configured to hold the collimator. The movement system is configured to move the second structure of the bearing system such that the second structure rotates in one of a plurality of directions substantially about a center point in the radiation source while the radiation source remains stationary relative to the second structure. Rotation of the second structure substantially about the center point changes a direction in which the beam formed by the collimator is directed.

Figure 1:
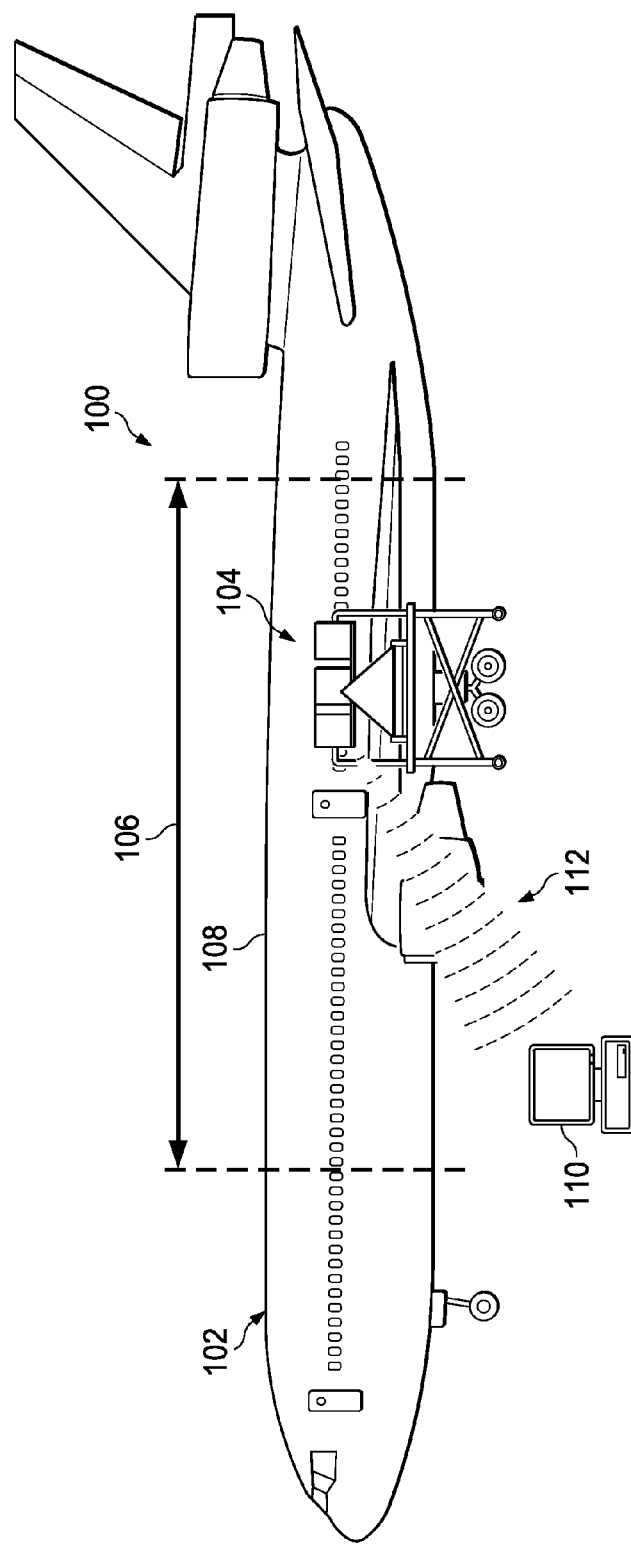
FIG. 1 is an illustration of an x-ray inspection environment in accordance with an illustrative embodiment.

With reference now to the figures and, in particular, with reference to FIG. 1, an illustration of an x-ray inspection environment is depicted in accordance with an illustrative embodiment. In this depicted example, x-ray inspection environment 100 includes aircraft 102 and backscatter x-ray system 104. In this illustrative example, backscatter x-ray system 104 is configured to inspect an object, such as, for example, fuselage 108 of aircraft 102. In particular, backscatter x-ray system 104 is used to inspect section 106 of fuselage 108 of aircraft 102 in this depicted example.

Backscatter x-ray system 104 may be positioned outside of fuselage 108 or inside of fuselage 108 to inspect section 106 of fuselage 108. In one illustrative example, backscatter x-ray system 104 is placed inside section 106 of fuselage 108 and configured to move within fuselage 108 to inspect section 106 of fuselage 108.

In particular, backscatter x-ray system 104 is configured to emit a single x-ray beam that is moved along section 106 in a selected pattern as backscatter x-ray system 104 moves within fuselage 108. For example, the x-ray beam may be directed at a location on section 106 of fuselage 108 and then moved or steered to scan section 106 of fuselage 108 in a selected pattern.

This x-ray beam may penetrate through at least a portion of the thickness of section 106 of fuselage 108 at the location at which the x-ray beam is directed. As used herein, "at least a portion" of an item or a plurality of items may be some or all of the items or plurality of items. For example, at least a portion of the thickness of section 106 may be some of this thickness or the entire thickness. In this illustrative example, the x-ray beam penetrates through the entire thickness of section 106 at the location at which the x-ray beam is directed.

When backscatter x-ray system 104 is located inside fuselage 108, a portion of the x-rays in the x-ray beam that encounter section 106 of fuselage 108 are scattered by section 106 of fuselage 108. These scattered x-rays are referred to as backscatter x-rays or backscatter.

In this illustrative example, backscatter x-ray system 104 is configured to detect this backscatter and use the detected backscatter to generate images of section 106 of fuselage 108. These images may be used as part of the inspection process to determine whether one or more inconsistencies are present in section 106 of fuselage 108. In particular, these images may be used to determine whether one or more inconsistencies are present on an interior surface of section 106, on an exterior surface of section 106, and/or between the interior surface and the exterior surface of section 106.

As depicted, the images generated by backscatter x-ray system 104 may be sent to computer system 110 over wireless communications link 112. Computer system 110 may process these images to determine whether one or more inconsistencies are present in section 106 of fuselage 108. Although wireless communications link 112 is used for communications between computer system 110 and backscatter x-ray system 104 in this depicted example, a wired communications link, an optical communications link, or some other suitable type of communications link may be used in other illustrative examples.

Figure 2:
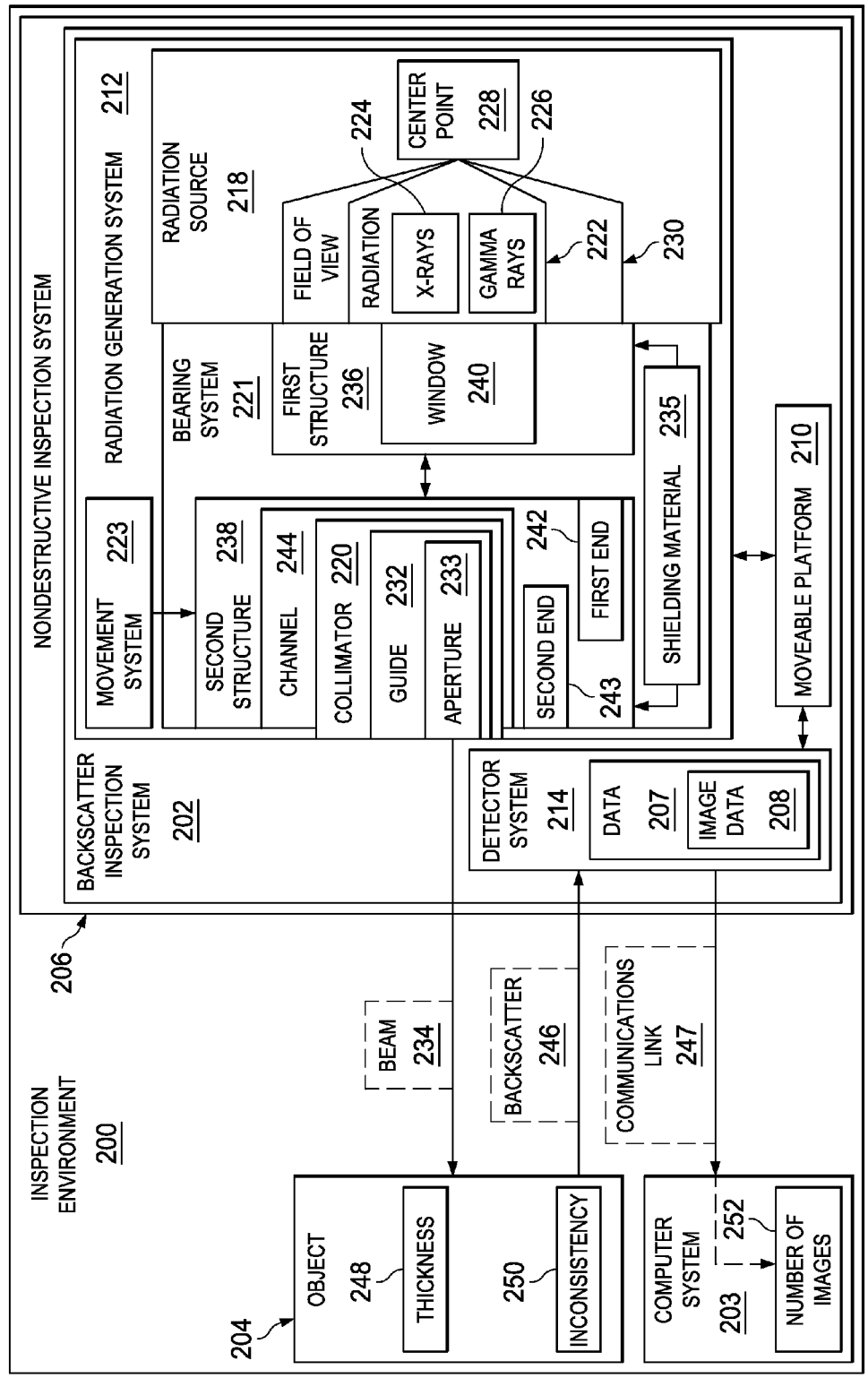
FIG. 2 is an illustration of an inspection environment in the form of a block diagram in accordance with an illustrative embodiment.

With reference now to FIG. 2, an illustration of an inspection environment in the form of a block diagram is depicted in accordance with an illustrative embodiment. X-ray inspection environment 100 in FIG. 1 is an example of one implementation for inspection environment 200 in FIG. 2.

In these illustrative examples, inspection environment 200 includes backscatter inspection system 202, computer system 203, and object 204. Backscatter inspection system 202 one example for nondestructive inspection (NDI) system 206. As used herein, a "nondestructive inspection system," such as nondestructive inspection system 206, is a system configured to inspect an object, such as object 204, without causing any undesired effects to the object. In particular, a nondestructive inspection system is configured to inspect an object without causing any physical alterations on the object.

Nondestructive inspection system 206 may also be referred to as a nondestructive evaluation (NDE) system, a nondestructive testing (NDT) system, or a nondestructive examination (NDE) system. Backscatter x-ray system 104 in FIG. 1 is an example of one implementation for nondestructive inspection system 206 in FIG. 2.

In these illustrative examples, backscatter inspection system 202 may be used to inspect object 204. Object 204 may be selected from any number of different types of objects. For example, without limitation, object 204 may take the form of a mobile platform, a stationary platform, an air-based structure, a land-based structure, an aquatic-based structure, a space-based structure, or some other suitable type of structure. More specifically, object 204 may be a an aircraft, a ship, a tank, a personnel carrier, a spacecraft, a space station, a satellite, a submarine, a vehicle, a manmade structure, a building, or some other suitable type of object.

In some cases, object 204 may be a part in another object. For example, in some cases, object 204 may be a section of a fuselage for an aircraft, a wing, a fuel tank, a structural support on a bridge, a section of a space station, the hull of a ship, a skin panel, a wall, a door, or some other suitable type of part.

Backscatter inspection system 202 generates data 207 for object 204 during inspection of object 204. Data 207 may include, for example, without limitation, image data 208 for object 204. Further, backscatter inspection system 202 sends data 207 to computer system 203. Computer system 203 is configured to receive and process data 207 generated by backscatter inspection system 202.

In this illustrative example, backscatter inspection system 202 includes moveable platform 210, radiation generation system 212, and detector system 214. In this illustrative example, radiation generation system 212 and detector system 214 are connected to moveable platform 210.

As used herein, a first component "connected to" a second component means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

Moveable platform 210 may be any platform configured to move over a surface. This movement may include translation and/or rotation. Moveable platform 210 may take various forms depending on the particular implementation. In one illustrative example, moveable platform 210 may be a cart.

Moveable platform 210 may include movement devices such as, for example, without limitation, wheels, rollers, sliders, a track system, and other types of movement devices. These movement devices may allow moveable platform 210 to move or be moved on a surface, such as, for example, without limitation, a floor, a rail system, or some other suitable type of surface.

In one illustrative example, moveable platform 210 may be moved by a human operator pushing moveable platform 210. In another illustrative example, moveable platform 210 may be moved using a propulsion system in moveable platform 210.

In these illustrative examples, radiation generation system 212 comprises radiation source 218, collimator 220, bearing system 221, and movement system 223. Radiation source 218 is configured to generate radiation 222. Radiation 222 comprises a plurality of rays. Radiation 222 may take a number of different forms. In these illustrative examples, radiation 222 may take the form of x-rays 224, gamma rays 226, or some other suitable type of radiation configured to penetrate object 204.

In one illustrative example, radiation source 218 takes the form of an x-ray tube configured to generate and emit x-rays 224. This x-ray tube may have a cylindrical shape.

Radiation source 218 emits radiation 222 from a point within radiation source 218. In one illustrative example, radiation source 218 may emit radiation 222 radially from center point 228 in radiation source 218. Center point 228 may be a point along a center axis through radiation source 218. When radiation source 218 has a cylindrical shape, center point 228 may be any point along a center axis along the length of the cylindrical shape. Of course, in other illustrative examples, center point 228 may be any point within an interior of radiation source 218. In some illustrative examples, radiation source 218 may emit radiation 222 from a point within radiation source 218 other than center point 228.

Radiation 222 is emitted by radiation source 218 within field of view (FOV) 230. As used herein, a "field of view" (FOV) for a radiation source, such as field of view 230 for radiation source 218, is the horizontal extent and vertical extent to which radiation 222 is emitted. In these illustrative examples, field of view 230 may be described using degrees in a horizontal direction and degrees in a vertical direction with respect to radiation source 218.

In these illustrative examples, collimator 220 is a device that filters the plurality of rays in radiation 222 such that only the portion of rays traveling parallel to a specified direction are allowed to pass through collimator 220. This specified direction may be the direction along a center axis through guide 232 in collimator 220. Guide 232 is a channel within collimator 220 through which rays may pass. In particular, collimator 220 may absorb a portion of the rays in radiation 222, scatter a portion of the rays in radiation 222, or perform a combination of the two such that only rays that travel in the direction of the center axis through guide 232 may pass through collimator 220.

A portion of radiation 222 that passes through guide 232 in collimator 220 exits collimator 220 at aperture 233 in the form of beam 234. Beam 234 may comprise one or more rays of radiation. Aperture 233 is an opening in collimator 220 at the end of guide 232. Beam 234 may exit aperture 233 in a direction toward object 204. In this manner, collimator 220 is configured to filter the rays in radiation 222 to form and emit beam 234. When radiation 222 takes the form of x-rays 224, beam 234 is referred to as an x-ray beam.

In some illustrative examples, collimator 220 may be configured to change the size of aperture 233 and/or the length of guide 232 in collimator 220. Changing the length of guide 232 may change the field intensity and/or beam dispersion of beam 234. For example, increasing the length of guide 232 decreases field intensity and decreases beam dispersion. Changing the size of aperture 233 changes the spot size of beam 234 on object 204.

Collimator 220, in these illustrative examples, is moveably connected to radiation source 218 using bearing system 221 associated with collimator 220. Bearing system 221 comprises one or more components that moveably connect collimator 220 to radiation source 218 in a manner that allows collimator 220 to move independently of radiation source 218. For example, bearing system 221 may allow collimator 220 to move around radiation source 218, while radiation source 218 remains stationary relative to collimator 220.

In these illustrative examples, bearing system 221 comprises first structure 236 and second structure 238. First structure 236 is associated with radiation source 218. When one component is "associated" with another component, the association is a physical association in these depicted examples. For example, a first component, such as first structure 236, may be considered to be associated with a second component, such as second structure 238, by being secured to the second component, bonded to the second component, mounted to the second component, welded to the second component, fastened to the second component, and/or connected to the second component in some other suitable manner.

The first component also may be connected to the second component using a third component. Additionally, the first component may be considered to be associated with the second component by being formed as part of and/or an extension of the second component.

In these illustrative examples, first structure 236 may be a structure that is associated with radiation source 218 by wrapping around at least a portion of radiation source 218. In one illustrative example, first structure 236 has a toroidal-type shape that surrounds the portion of radiation source 218 from which radiation 222 is emitted. A toroidal-type shape is a ring-type shape with a hollow center portion.

In this illustrative example, the hollow center portion of first structure 236 may substantially conform to the curved shape of radiation source 218 such that first structure 236 wraps around radiation source 218. In some cases, center point 228 of radiation source 218 may also be a center point for first structure 236.

In another illustrative example, first structure 236 may only be a section of a toroidal-type shape. For example, first structure 236 may have an arc-type shape that substantially conforms to the curved shape of a portion of radiation source 218.

In these illustrative examples, first structure 236 has window 240 through which at least a portion of radiation 222 is allowed to pass without being scattered, absorbed, or a combination of the two. When all of radiation 222 is allowed to pass through window 240, window 240 may have a size and shape selected based on field of view 230 for radiation source 218.

Further, in these examples, window 240 may be comprised of a material that allows radiation 222 to pass through window 240 without any of radiation 222 being scattered and/or absorbed. However, in some cases, window 240 may be an opening in first structure 236. For example, window 240 may take the form of an open channel.

As depicted, second structure 238 has first end 242 and second end 243. Second structure 238 has a concave spherical shape at first end 242 of second structure 238 and an elongate shape at second end 243 of second structure 238. Further, second structure 238 has channel 244 that runs along a center axis through second structure 238. Channel 244 extends from first end 242 to second end 243 of second structure 238.

The size and/or shape of channel 244 may change along the length of second structure 238, depending on the implementation. For example, the portion of channel 244 at second end 243 of second structure 238 may be configured to receive and hold at least a portion of collimator 220 within channel 244.

In these illustrative examples, a portion of the rays in radiation 222 that pass through window 240 in first structure 236 pass through channel 244 in second structure 238. Further, a portion of the rays that pass through channel 244 in second structure 238, encounter the opening into guide 232 of collimator 220, and travel in a direction substantially parallel to a center axis through guide 232 may pass through guide 232. A portion of the rays that pass through guide 232 may exit aperture 233 in the form of beam 234.

In these illustrative examples, at least a portion of first structure 236 and second structure 238 comprises shielding material 235. Shielding material 235 is configured to scatter and/or absorb radiation 222 such that radiation 222 does not pass through shielding material 235. In particular, shielding material 235 is configured to protect the environment outside of radiation generation system 212 from any portion of radiation 222 that is not used to form beam 234. Shielding material 235 may comprise, for example, without limitation, at least one of lead, tungsten, brass, and some other suitable type of shielding material.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; or some other suitable combination.

Second structure 238 is connected to first structure 236. However, depending on the implementation, second structure 238 may or may not be moveably connected to first structure 236. In one illustrative example, the connection between second structure 238 and first structure 236 is a fixed connection. In particular, second structure 238 may not move independently of first structure 236. In other words, movement of second structure 238 causes movement of first structure 236.

In another illustrative example, second structure 238 is moveably connected to first structure 236. In this illustrative example, first structure 236 remains stationary relative to second structure 238 when second structure 238 moves.

Bearing system 221 is configured to allow second structure 238 to rotate substantially about center point 228 in radiation source 218. Depending on the implementation, center point 228 about which second structure 238 is rotated may or may not be the same point within radiation source 218 from which radiation 222 is emitted.

In these illustrative examples, bearing system 221 allows second structure 238 to rotate substantially in one of a plurality of directions about center point 228. When the connection between second structure 238 and first structure 236 is a fixed connection, rotation of second structure 238 in a particular direction substantially about center point 228 also causes first structure 236 to rotate in that particular direction substantially about center point 228.

When second structure 238 is moveably connected to first structure 236, first structure 236 remains stationary while second structure 238 is rotated substantially about center point 228 around first structure 236. In this manner, bearing system 221 is always configured to allow second structure 238 to rotate substantially about center point 228. However, bearing system 221 is configured to restrict the number of degrees by which second structure 238 may be rotated substantially about center point 228. Restriction of the movement of second structure 238 also restricts movement of first structure 236 when the connection between these two structures is a fixed connection.

As one illustrative example, second structure 238 and/or first structure 236 may be rotated in any direction substantially about center point 228 but within a selected range of degrees. This selected range of degrees may be less than about 360 degrees. In some cases, this selected range may be less than about 180 degrees.

Movement system 223 is configured to move bearing system 221. In particular, movement system 223 is configured to move second structure 238 such that second structure 238 rotates around radiation source 218 substantially about center point 228. This movement of second structure 238 causes collimator 220 held by second structure 238 to also rotate. When collimator 220 moves, beam 234 moves.

Movement system 223 may also be used to restrict the movement of second structure 238. In one illustrative example, bearing system 221 and movement system 223 may be configured such that rotation of second structure 238 is restricted to within field of view 230 for radiation source 218. In other words, the extent to which second structure 238 may be rotated in any direction substantially about center point 228 may not be greater than the extent of field of view 230 for radiation source 218 in that direction. In this illustrative example, collimator 220 may be rotated such that beam 234 may be directed or pointed in any direction within field of view 230 for radiation source 218.

The movement of second structure 238 and first structure 236 may be restricted such that shielding material 235 may not be required to wrap around all of radiation source 218. Rather, shielding material 235 in first structure 236 may only be needed around the portion of radiation source 218 at which radiation 222 is emitted.

In some illustrative examples, one or more components in movement system 223 may be connected to moveable platform 210. Of course, in other illustrative examples, one or more components in movement system 223 may be connected to radiation source 218. In still other illustrative examples, movement system 223 may be connected to some other structure within backscatter inspection system 202.

Movement system 223 may comprise a number of devices configured to move bearing system 221. For example, movement system 223 may include at least one of an actuator, a gear, a motor, a track system, and/or other suitable types of devices.

Beam 234 may be directed toward object 204 to perform inspection of object 204. In these illustrative examples, object 204, moveable platform 210, and/or bearing system 221 with collimator 220 may be moved such that beam 234 may be moved along object 204 in a selected pattern. This selected pattern may be, for example, a raster pattern, a step pattern, a sinusoidal pattern, or some other suitable type of pattern.

With a raster pattern, beam 234 may be moved back and forth in a number of directions parallel to each other. In this manner, beam 234 may be moved along object 204 such that the rays in beam 234 penetrate through different locations along object 204.

In these illustrative examples, bearing system 221 is configured to move independently of radiation source 218. In other words, radiation source 218 remains stationary relative to bearing system 221 when movement system 223 moves second structure 238 to steer beam 234.

At each location on object 204 at which beam 234 is directed, beam 234 penetrates through at least a portion of thickness 248 of object 204. At least a portion of the rays in beam 234 may be scattered when beam 234 encounters object 204. For example, these scattered rays may include rays scattered by a surface of object 204 and/or scattered by a subsurface portion of object 204 beneath the surface of object 204. The scattered rays formed by beam 234 encountering object 204 form backscatter 246.

Detector system 214 in backscatter inspection system 202 is configured to detect backscatter 246. Detector system 214 may take a number of different forms. For example, detector system 214 may include one or more detectors. A detector in detector system 214 may comprise at least one of, for example, without limitation, a solid state detector, a scintillator detector, and some other suitable type of detector.

Detector system 214 generates data 207 in response to detecting backscatter 246. Image data 208 in data 207 may include, for example, a value for a pixel corresponding to each of a plurality of locations on object 204 at which beam 234 was directed.

Detector system 214 sends data 207 to computer system 203 for processing using communications link 247. Communications link 247 may be a wireless communications link, a wired communications link, an optical communications link, or some other suitable type of communications link.

Computer system 203 may include one or more computers, depending on the implementation. As used herein, a "number of" when used with reference to items means one or more items. For example, a number of computers is one or more computers. When more than one computer is present in computer system 203, these computers may be in communication with each other using a medium such as a network. The network may employ wired communications links, wireless communications links, and other suitable types of links for exchanging information.

Data 207 may be used to determine whether inconsistency 250 is present in object 204. Inconsistency 250 may be present at the surface of object 204 or within an interior of object 204. In one illustrative example, computer system 203 uses data 207 to form number of images 252 of object 204. Number of images 252 may be analyzed by computer system 203 and/or a human operator to detect the presence of, and identify the location of, inconsistency 250 in object 204. Of course, in other illustrative examples, image data 208 in data 207 generated by detector system 214 may take the form of number of images 252.

Depending on the implementation, computer system 203 may be configured to control at least one of radiation generation system 212, moveable platform 210, and detector system 214. For example, computer system 203 may send commands to moveable platform 210 and/or movement system 223 in radiation generation system 212 to control the steering of beam 234. In some cases, computer system 203 may send commands to radiation generation system 212 to control the size of aperture 233 and/or the length of guide 232 in collimator 220.

The configuration of radiation source 218, collimator 220, bearing system 221, and movement system 223 in radiation generation system 212 in FIG. 2 provides a radiation generation system with a lower level of complexity as compared to radiation generation systems in some currently used nondestructive inspection systems. Further, with collimator 220 being moveably connected to radiation source 218 using bearing system 221, backscatter inspection system 202 may be reduced in size as compared to other currently used backscatter inspection systems. As a result of the reduction in complexity and size, backscatter inspection system 202 may weigh less than currently used backscatter inspection systems.

Thus, backscatter inspection system 202 may be used to inspect many different locations such as, for example, without limitation, interior locations and other locations that may be hard to reach using currently available backscatter inspection systems. For example, when object 204 is a fuel tank in an aircraft, backscatter inspection system 202 may have a size and configuration that allows backscatter inspection system 202 to be placed within the fuel tank to inspect the fuel tank from within the fuel tank.

Additionally, the reduced size and weight of backscatter inspection system 202 may allow an operator to more easily move backscatter inspection system 202 and/or maneuver around backscatter inspection system 202. Consequently, backscatter inspection system 202 may provide more cost savings for the operator and/or increase the efficiency with which inspections are performed as compared to some currently used x-ray inspections systems.

The illustration of inspection environment 200 in FIG. 2 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

In some illustrative examples, moveable platform 210 may take the form of a housing or unit in which radiation generation system 212 and detector system 214 may be placed. This housing system may be moveable by a robotic arm or some other system. In some illustrative examples, computer system 203 may be considered part of backscatter inspection system 202 and/or located on moveable platform 210.

In one illustrative example, computer system 203 may analyze data 207 and generate an identification of inconsistency 250 when inconsistency 250 is detected on the surface of object 204. In another illustrative example, bearing system 221 and collimator 220 both may be considered part of a collimator assembly. In some cases, first structure 236 of bearing system 221 may be referred to as a collar or a collimator collar.

Figure 3:
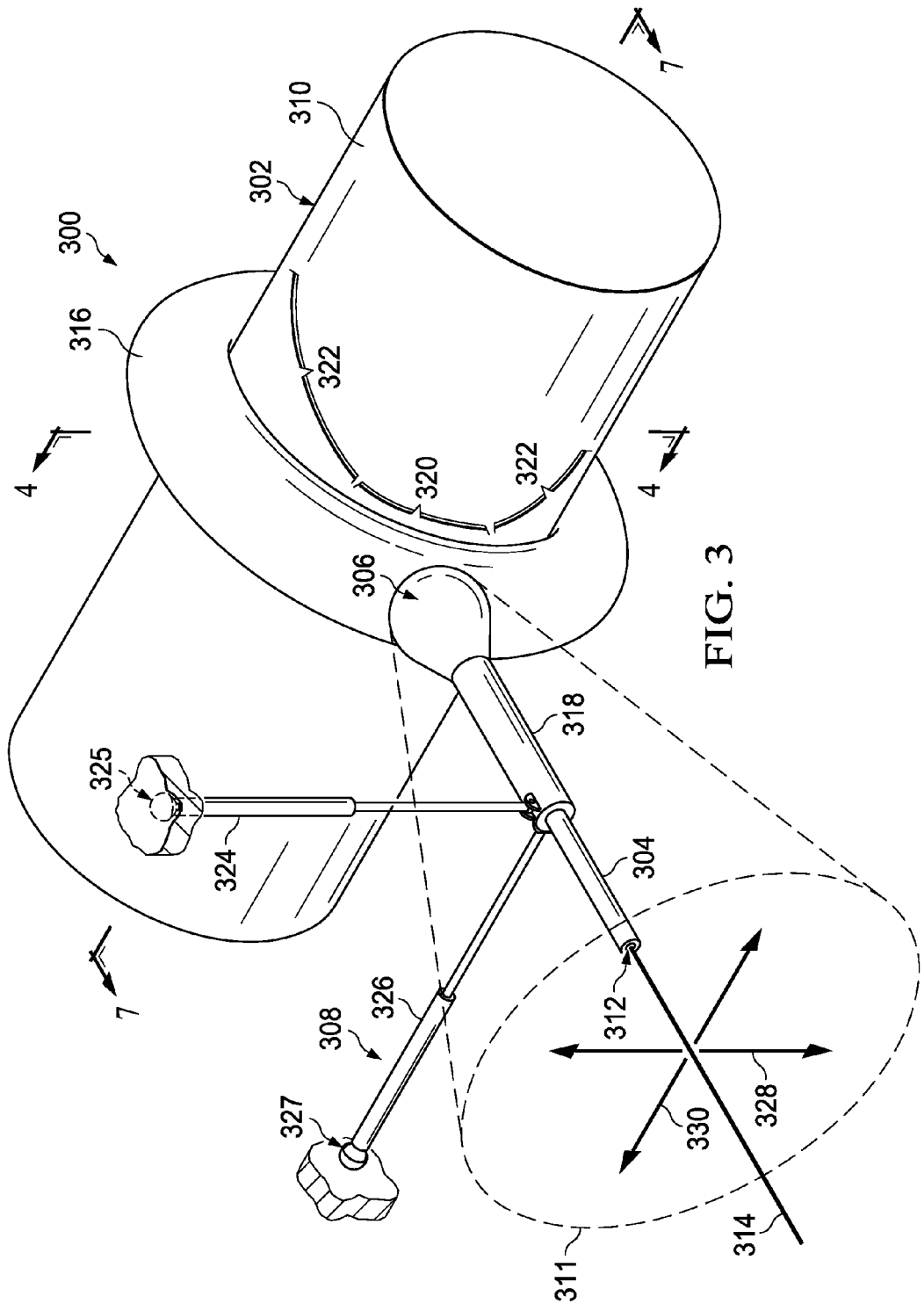
FIG. 3 is an illustration of a perspective view of a radiation generation system in accordance with an illustrative embodiment.

With reference now to FIG. 3, an illustration of a perspective view of a radiation generation system is depicted in accordance with an illustrative embodiment. In this illustrative example, radiation generation system 300 is an example of one implementation for radiation generation system 212 in FIG. 2.

As depicted, radiation generation system 300 comprises radiation source 302, collimator 304, bearing system 306, and movement system 308. Radiation source 302, collimator 304, bearing system 306, and movement system 308 are examples of implementations for radiation source 218, collimator 220, bearing system 221, and movement system 223 in FIG. 2. Radiation generation system 300 may be connected to a moveable platform (not shown), such as, for example, moveable platform 210 in FIG. 2.

In this illustrative example, radiation generation system 300 is an x-ray system and radiation source 302 takes the form of x-ray tube 310. X-ray tube 310 generates x-rays (not shown) within field of view 311 for x-ray tube 310. Collimator 304 filters these x-rays such that only a portion of these x-rays is allowed to exit aperture 312 of collimator 304. In particular, the portion of x-rays that exits aperture 312 of collimator 304 forms x-ray beam 314.

Bearing system 306 connects collimator 304 to x-ray tube 310. As depicted, bearing system 306 comprises first structure 316 and second structure 318. In this illustrative example, first structure 316 has a toroidal-type shape. First portion 320 of first structure 316 is comprised of a shielding material, while second portion 322 of first structure 316 is comprised of a material that is lighter than a shielding material. Second structure 318 is also comprised of this shielding material in this illustrative example.

Second structure 318 has an elongate shape configured to hold collimator 304. Second structure 318 is moveably connected to first structure 316 in this illustrative example. In particular, second structure 318 is configured to move independently of first structure 316. More specifically, when second structure 318 is moved, first structure 316 remains stationary relative to second structure 318.

Movement system 308 is configured to move bearing system 306. In particular, movement system 308 is configured to move second structure 318 of bearing system 306. In this illustrative example, movement system 308 comprises first actuator 324 and second actuator 326. First actuator 324 and second actuator 326 may be connected to a moveable platform (not shown) for radiation generation system 300.

For example, first actuator 324 and second actuator 326 may be connected to the moveable platform by bearing 325 and bearing 327, respectively. Bearing 325 and bearing 327 are spherical bearings in this illustrative example. Of course, in other illustrative examples, first actuator 324 and second actuator 326 may be connected to some other suitable type of structure using bearing 325 and bearing 327, respectively.

First actuator 324 is configured to lengthen or shorten to rotate second structure 318 around first structure 316 and x-ray tube 310. Similarly, second actuator 326 is configured to lengthen or shorten to rotate second structure 318 around first structure 316 and x-ray tube 310.

First actuator 324 and second actuator 326 may be operated together. For example, first actuator 324 and second actuator 326 may both be lengthened or both be shortened. Further, in some cases, first actuator 324 may be shortened, while second actuator 326 is lengthened. In other cases, first actuator 324 may be lengthened, while second actuator 326 is shortened. In particular, first actuator 324 and/or second actuator 326 may be operated to rotate second structure 318 such that the location on an object at which x-ray beam 314 is pointed moves in at least one of a direction along axis 328 and a direction along axis 330.

The extent to which the length of first actuator 324 and the length of second actuator 326 can be changed determines the range of rotation for second structure 318. Further, the shape and/or size of first structure 316 and second structure 318 may be configured to restrict the range of rotation for second structure 318. In this illustrative example, second structure 318 may be rotated around first structure 316 such that x-ray beam 314 may be directed in any direction within field of view 311 for x-ray tube 310. In other illustrative examples, x-ray beam 314 may be directed in any direction within only a portion of field of view 311.

Figure 4:
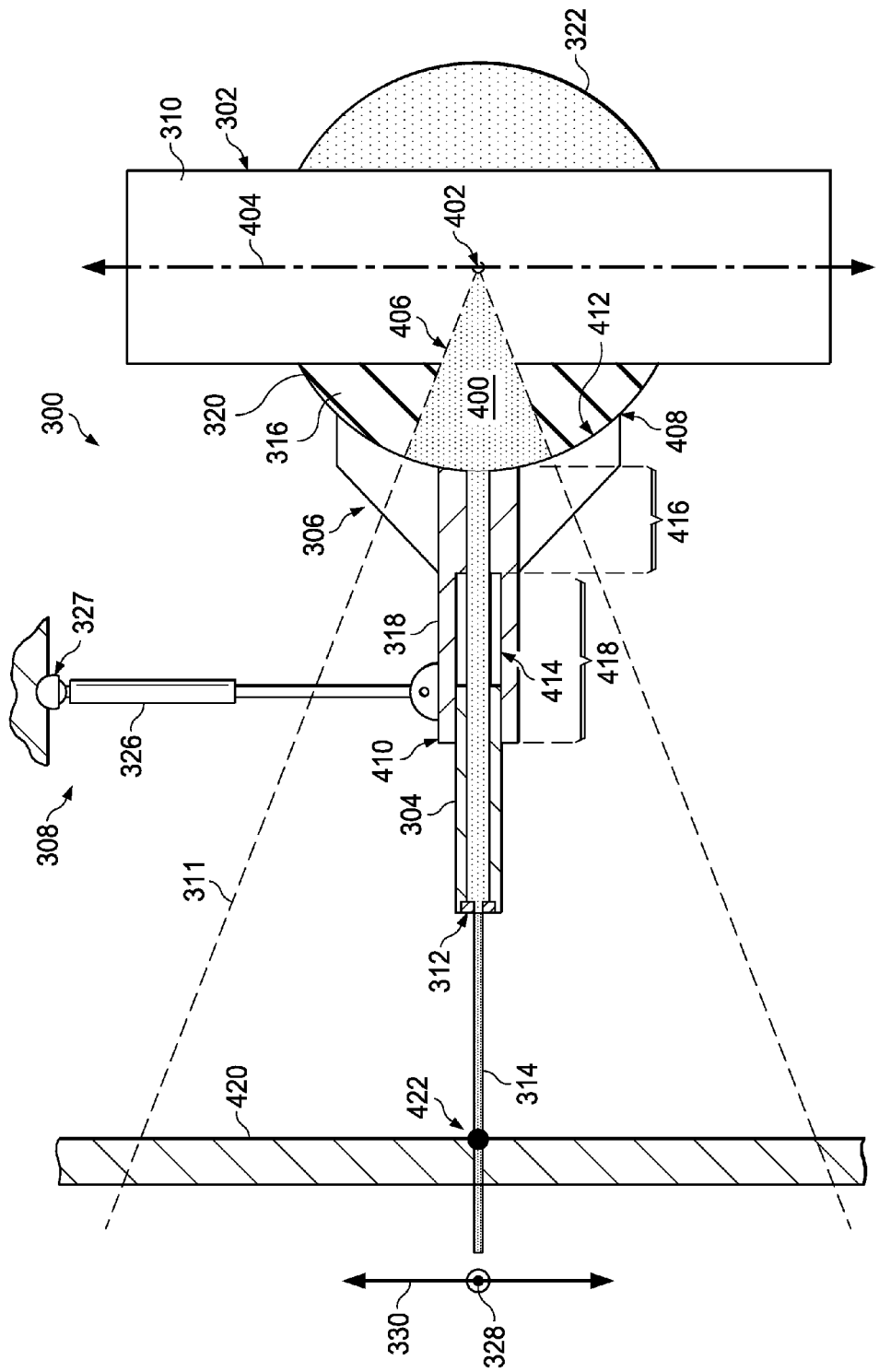
FIG. 4 is an illustration of a cross-sectional view of a radiation generation system in accordance with an illustrative embodiment.
Figure 5:
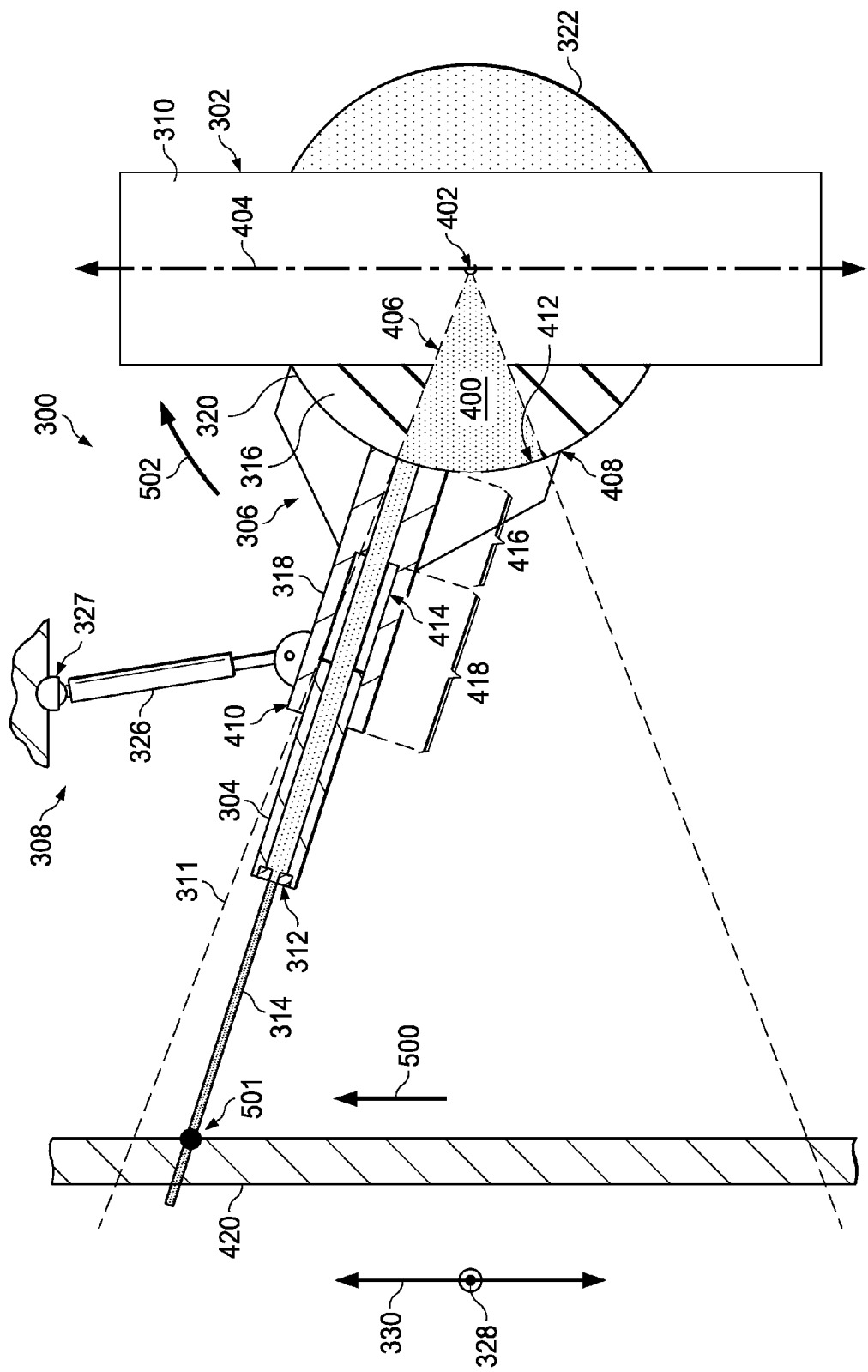
FIG. 5 is an illustration of a cross-sectional view of a radiation generation system in accordance with an illustrative embodiment.
Figure 6:
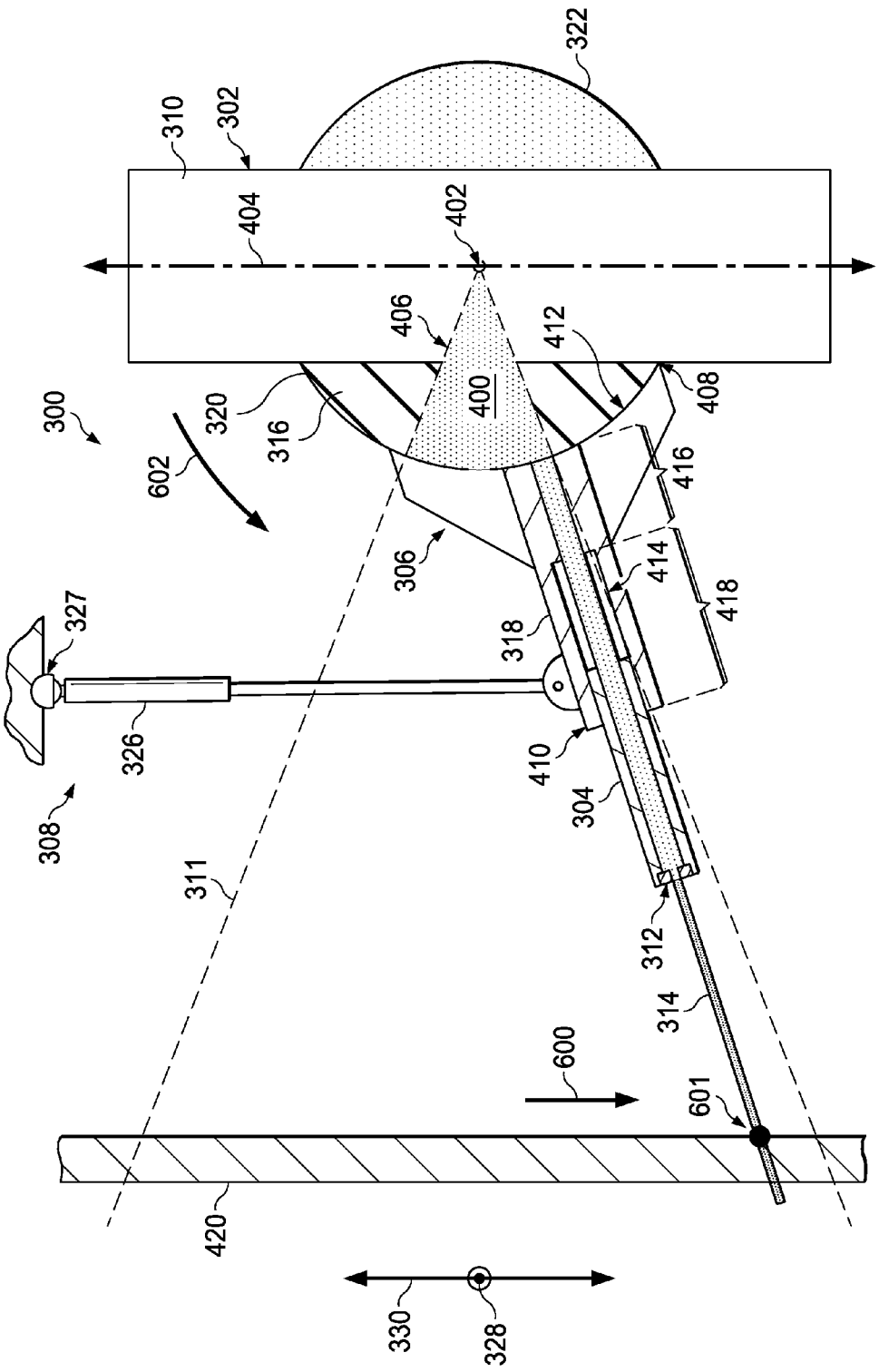
FIG. 6 is an illustration of a cross-sectional view of a radiation generation system in accordance with an illustrative embodiment.

With reference now to FIGS. 4-6, illustrations of a cross-sectional view of radiation generation system 300 in FIG. 3, taken along lines 4-4 in FIG. 3, are depicted in accordance with an illustrative embodiment. First actuator 324 is not seen in the cross-sectional view of radiation generation system 300 in FIGS. 4-6.

Turning now to FIG. 4, x-ray tube 310 generates x-rays 400 and emits x-rays 400 from center point 402 along center axis 404 through x-ray tube 310. In this illustrative example, first structure 316 shares center point 402 with x-ray tube 310. In other words, first structure 316 and x-ray tube 310 may be substantially concentric to each other.

Further, first structure 316 has window 406 that allows substantially all of x-rays 400 to pass through first structure 316. As depicted, bearing system 306 provides shielding for the portion of x-rays 400 generated by x-ray tube 310 that do not form x-ray beam 314.

Second structure 318 is moveably connected to first structure 316 such that second structure 318 may rotate around first structure 316, while first structure 316 remains stationary. For example, second structure 318 has first end 408 and second end 410. First end 408 has concave spherical shape 412. With this shape, second structure 318 may rotate around first structure 316 in any direction substantially about center point 402.

Additionally, second structure 318 has channel 414 that extends through the entire length of second structure 318. First portion 416 of channel 414 is smaller than second portion 418 of channel 414. Second portion 418 of channel 414 has a size configured to receive and hold collimator 304 at second end 410 of second structure 318.

In this illustrative example, second structure 318 of bearing system 306 and collimator 304 are configured such that collimator 304 emits x-ray beam 314. Further, the size of aperture 312 and/or the length of collimator 304 may be changed to adjust x-ray beam 314.

As depicted, radiation generation system 300 emits x-ray beam 314 toward object 420 to perform inspection of object 420. In one illustrative example, object 420 may be a portion of a fuselage of an aircraft. In FIG. 4, x-ray beam 314 is pointed at location 422 on object 420.

Location 422 on object 420 at which x-ray beam 314 is pointed may be moved by at least one of operating movement system 308 and moving the moveable platform (not shown) to which radiation generation system 300 is connected. For example, second actuator 326 and/or first actuator 324 in FIG. 3 may be each lengthened or shortened to rotate second structure 318 around first structure 316 and x-ray tube 310 about center point 402 such that location 422 on object 420 at which x-ray beam 314 is pointed moves in a direction along axis 330.

Turning now to FIG. 5, movement system 308 has been operated such that location 422 on object 420 at which x-ray beam 314 was pointed in FIG. 4 has been moved in the direction of arrow 500 to location 501. In particular, second structure 318 has been rotated about center point 402 in the direction of arrow 502 to change the direction in which x-ray beam 314 is pointing.

As depicted, x-ray beam 314 is pointing in a direction at the furthest extent of field of view 311. Further, bearing system 306 provides shielding for the portion of x-rays 400 generated by x-ray tube 310 that do not form x-ray beam 314 even after rotation of second structure 318 in the direction of arrow 502.

Turning now to FIG. 6, movement system 308 has been operated such that location 422 on object 420 at which x-ray beam 314 is pointed in FIG. 4 has been moved in the direction of arrow 600 to location 601. In particular, second structure 318 has been rotated about center point 402 in the direction of arrow 602 to change the direction in which x-ray beam 314 is pointing.

As depicted, x-ray beam 314 is pointing in a direction at the furthest extent of field of view 311. Further, bearing system 306 provides shielding for the portion of x-rays 400 generated by x-ray tube 310 that do not form x-ray beam 314 even after rotation of second structure 318 in the direction of arrow 602.

Figure 7:
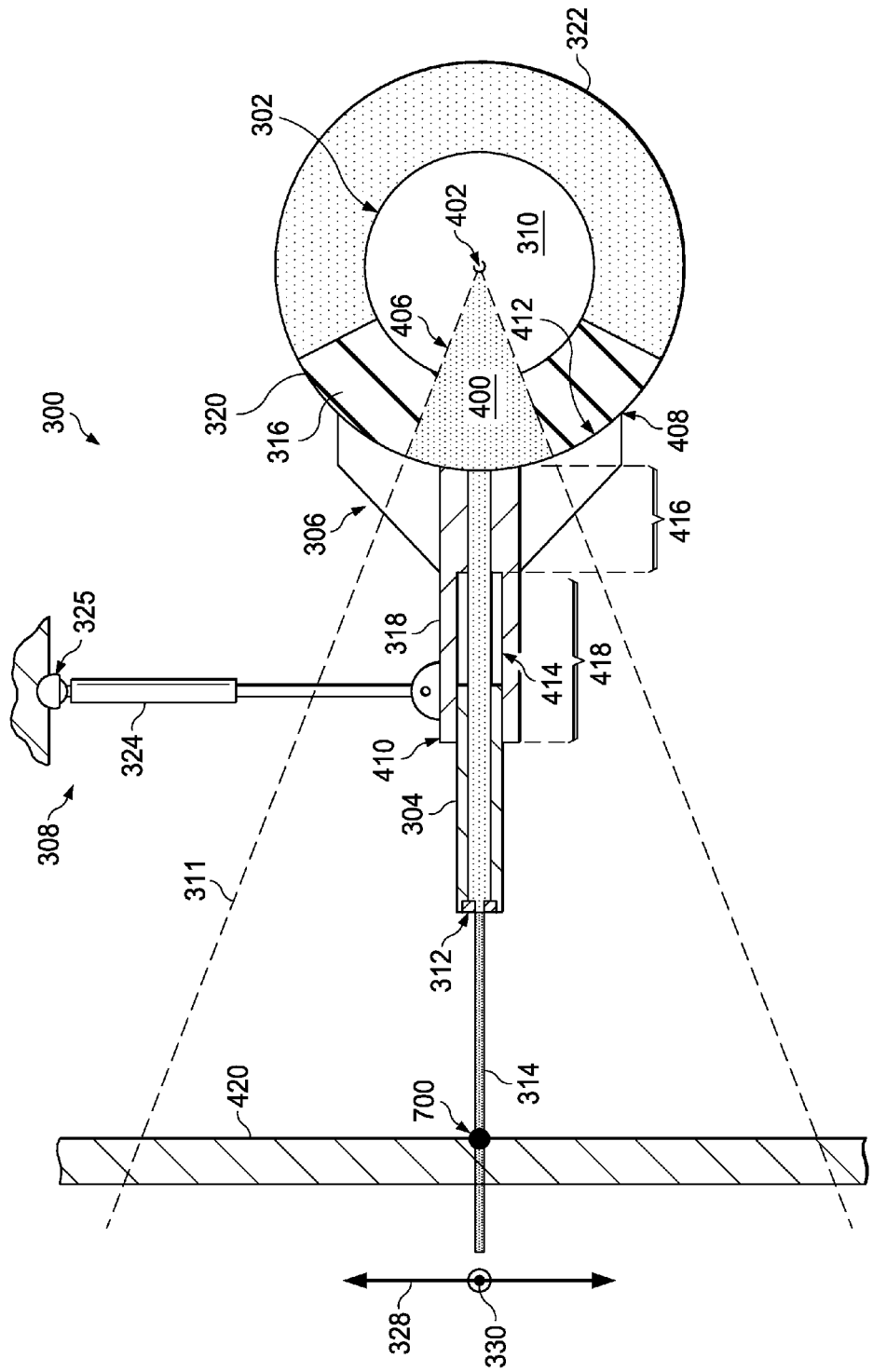
FIG. 7 is an illustration of a cross-sectional view of a radiation generation system in accordance with an illustrative embodiment.
Figure 8:
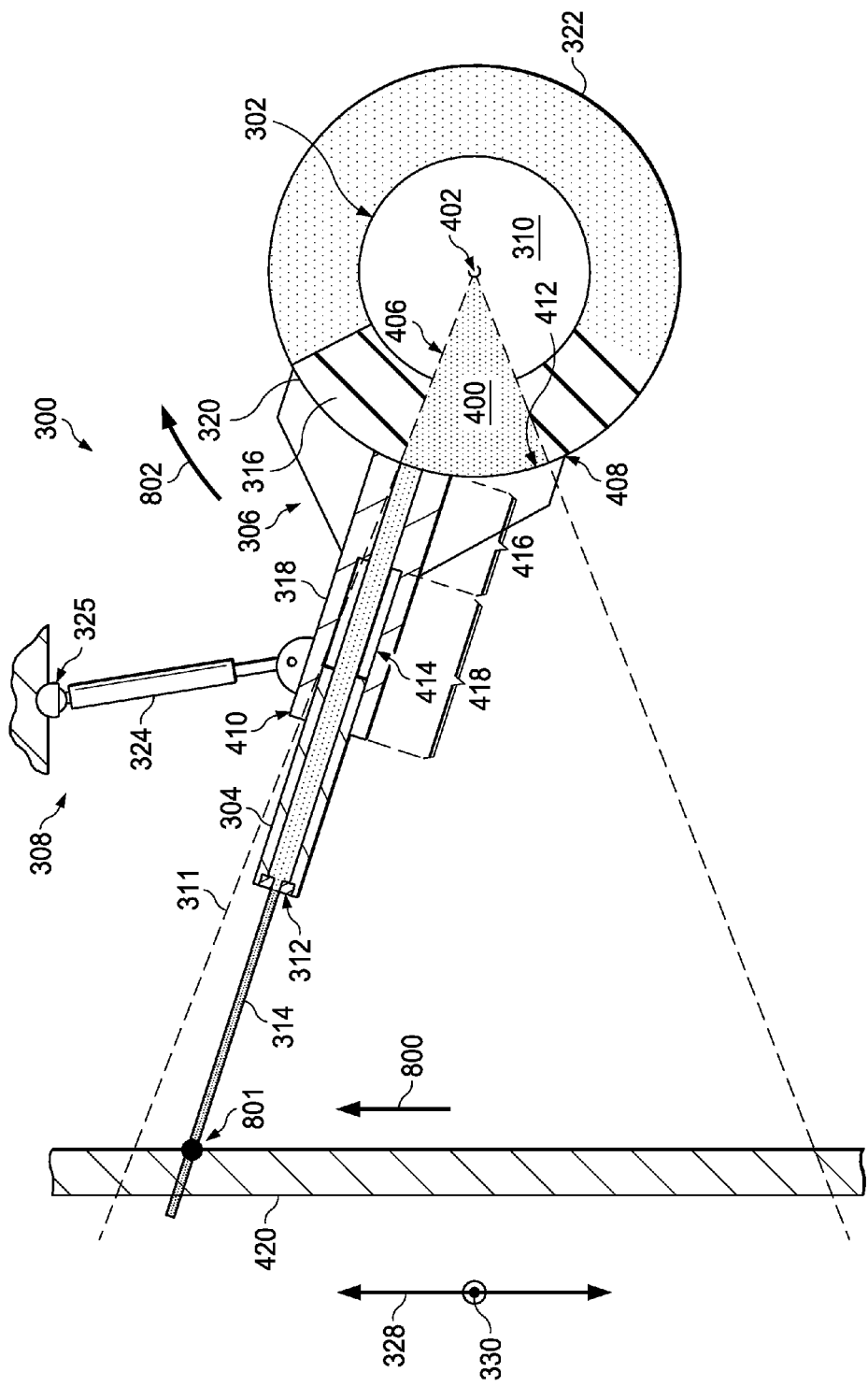
FIG. 8 is an illustration of a cross-sectional view of a radiation generation system in accordance with an illustrative embodiment.
Figure 9:
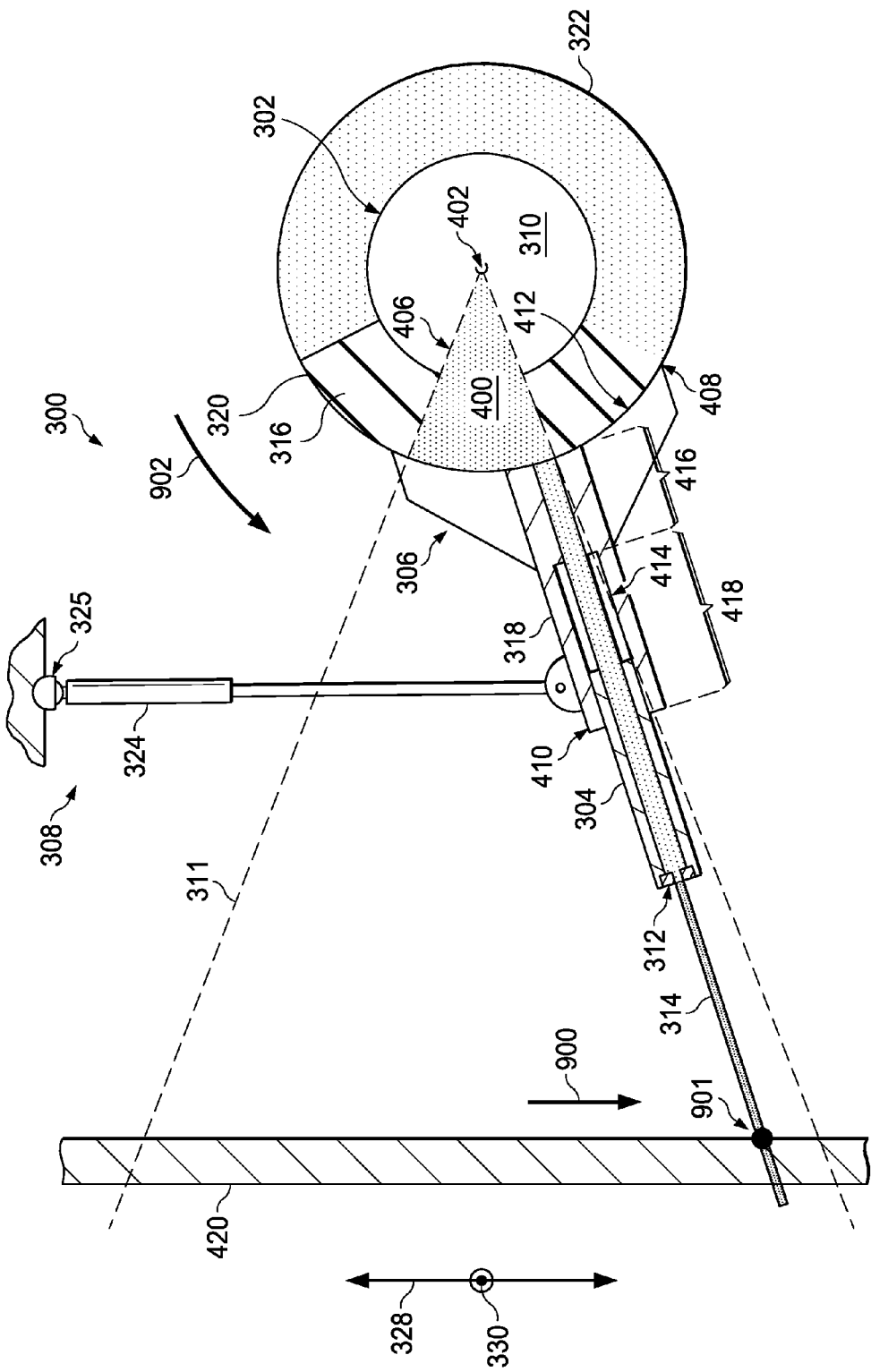
FIG. 9 is an illustration of a cross-sectional view of a radiation generation system in accordance with an illustrative embodiment.

With reference now to FIGS. 7-9, illustrations of a cross-sectional view of radiation generation system 300 in FIG. 3, taken along lines 7-7 in FIG. 3, are depicted in accordance with an illustrative embodiment. Second actuator 326 is not seen in the cross-sectional view of radiation generation system 300 in FIGS. 7-9.

Turning now to FIG. 7, x-ray tube 310 generates x-rays 400 and emits x-rays 400 from center point 402. In this illustrative example, x-ray beam 314 is pointed at location 700 on object 420.

Referring now to FIG. 8, movement system 308 has been operated such that location 700 on object 420 at which x-ray beam 314 is pointed in FIG. 7 has been moved in the direction of arrow 800 to location 801. In particular, second structure 318 has been rotated about center point 402 in the direction of arrow 802 to change the direction in which x-ray beam 314 is pointing.

As depicted, x-ray beam 314 is pointing in a direction at the furthest extent of field of view 311. Further, bearing system 306 provides shielding for the portion of x-rays 400 generated by x-ray tube 310 that do not form x-ray beam 314 even after rotation of second structure 318 in the direction of arrow 802.

Turning now to FIG. 9, movement system 308 has been operated such that location 700 on object 420 at which x-ray beam 314 is pointed in FIG. 7 has been moved in the direction of arrow 900 to location 901. In particular, second structure 318 has been rotated about center point 402 in the direction of arrow 902 to change the direction in which x-ray beam 314 is pointing.

As depicted, x-ray beam 314 is pointing in a direction at the furthest extent of field of view 311. Further, bearing system 306 provides shielding for the portion of x-rays 400 generated by x-ray tube 310 that do not form x-ray beam 314 even after rotation of second structure 318 in the direction of arrow 902.

Figure 10:
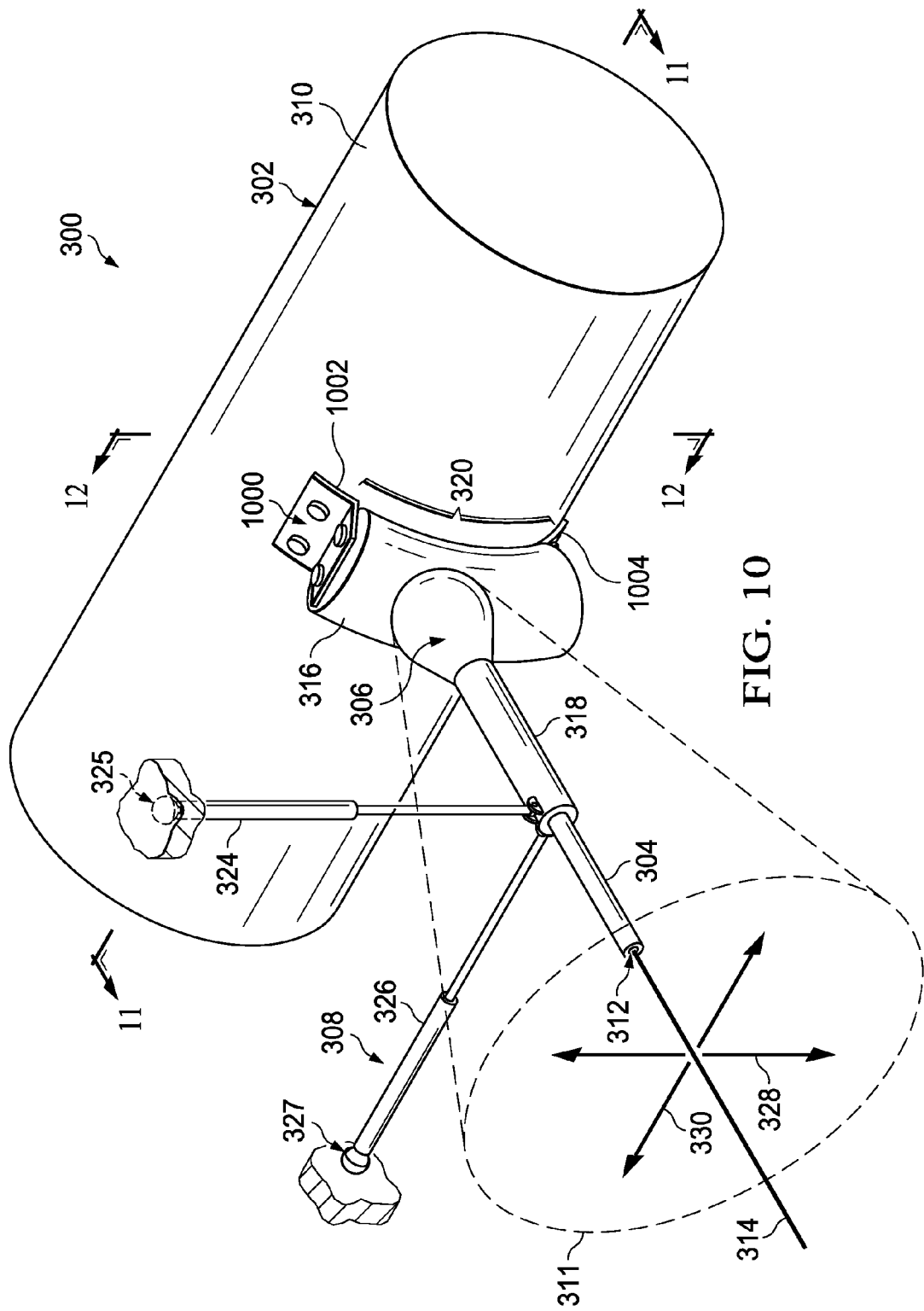
FIG. 10 is an illustration of a configuration for a bearing system in a radiation generation system in accordance with an illustrative embodiment.

With reference now to FIG. 10, an illustration of another configuration for bearing system 306 in radiation generation system 300 from FIGS. 3-9 is depicted in accordance with an illustrative embodiment. In this illustrative example, first structure 316 of bearing system 306 only has first portion 320. Second portion 322 of bearing system 306 in FIGS. 3-9 has been removed from first structure 316 of bearing system 306. In this manner, the weight and/or cost of bearing system 306 may be reduced.

Fastener system 1000 is used to attach first structure 316 to x-ray tube 310 in this illustrative example. As depicted, fastener system 1000 comprises fastening device 1002 and fastening device 1004.

Figure 11:
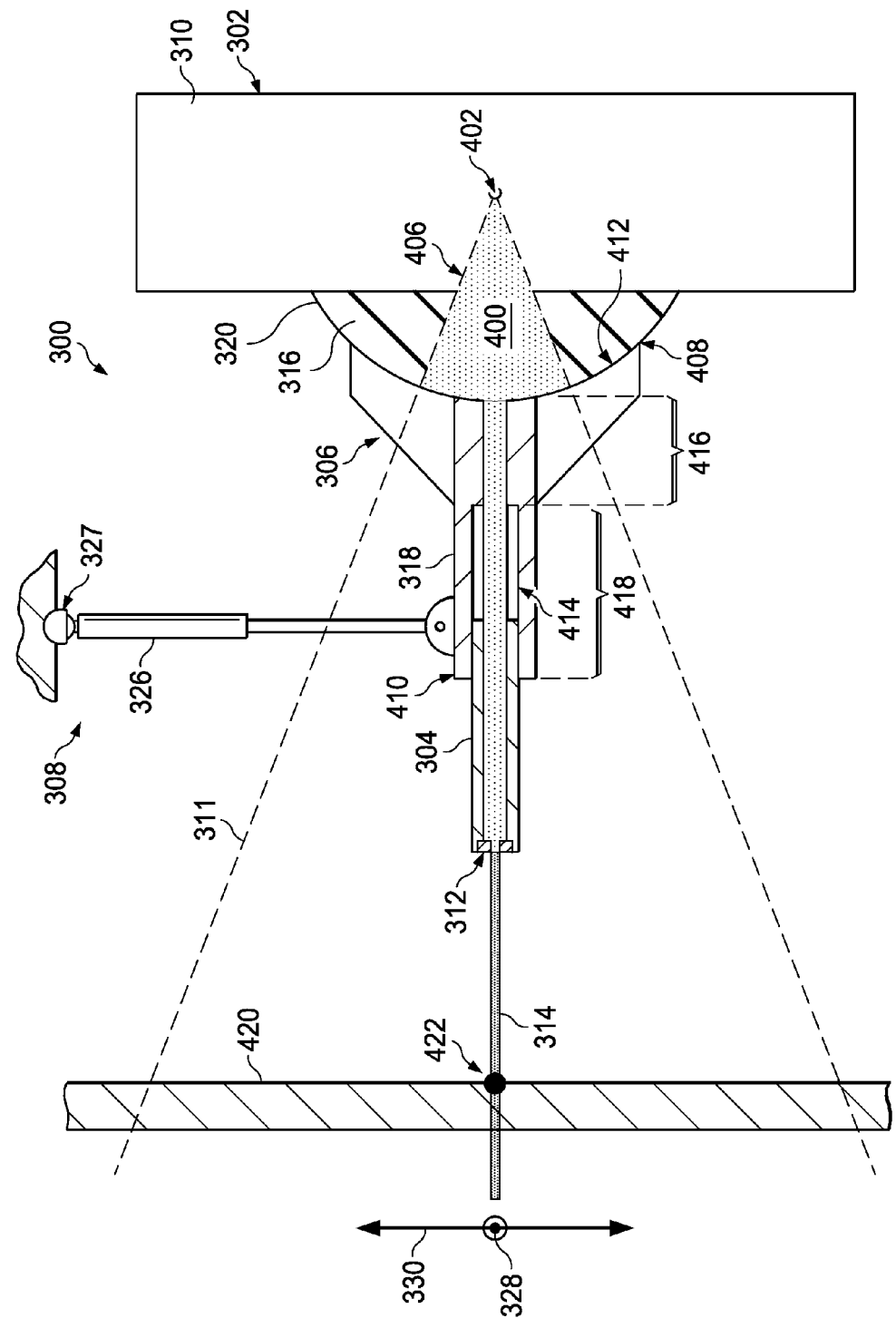
FIG. 11 is an illustration of a cross-sectional view of a radiation generation system in accordance with an illustrative embodiment.

Turning now to FIG. 11, an illustration of a cross-sectional view of radiation generation system 300 in FIG. 10 taken along lines 11-11 is depicted in accordance with an illustrative embodiment. As depicted, bearing system 306 does not wrap around all of x-ray tube 310.

Figure 12:
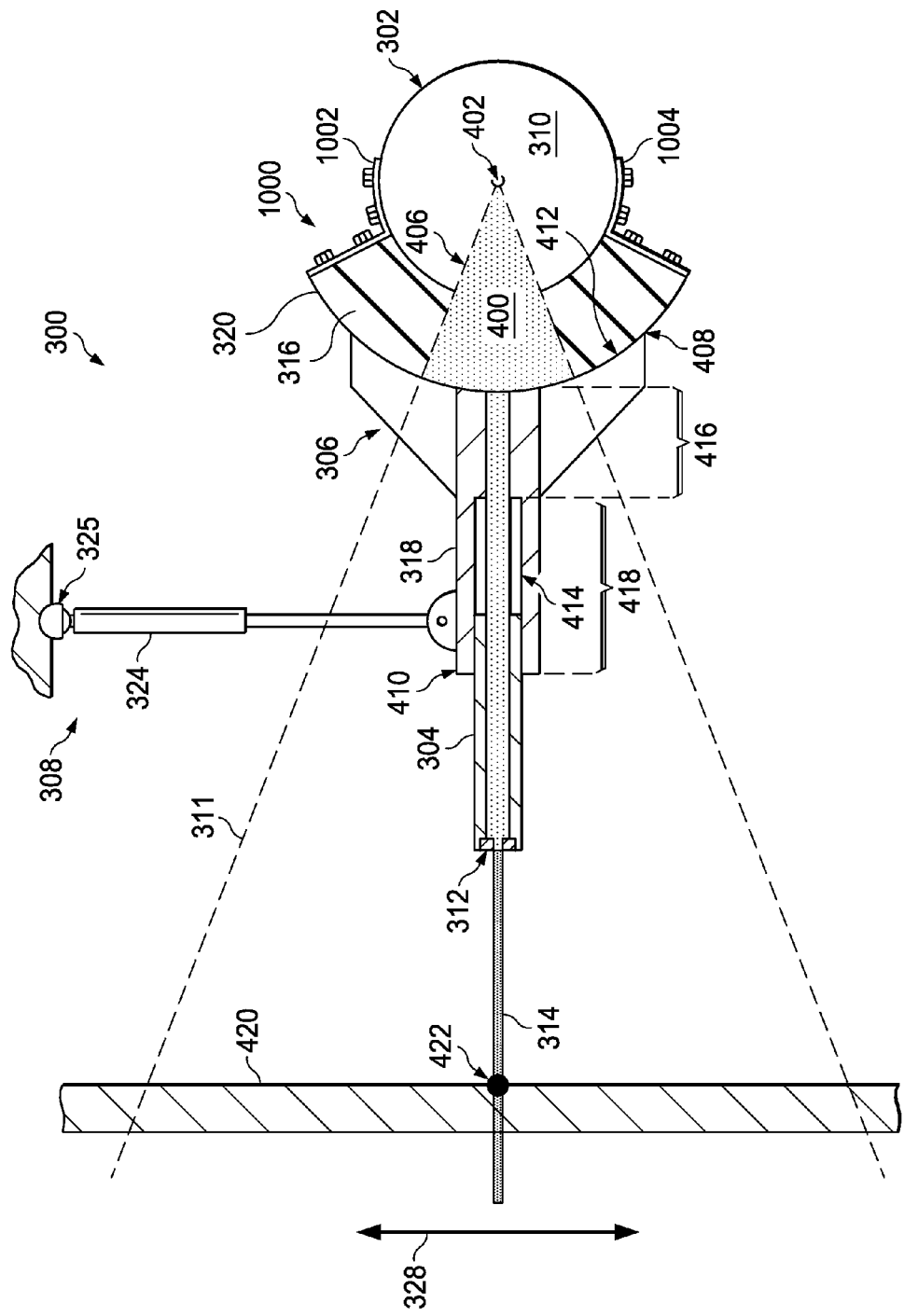
FIG. 12 is an illustration of a cross-sectional view of a radiation generation system in accordance with an illustrative embodiment.

Referring now to FIG. 12, an illustration of a cross-sectional view of radiation generation system 300 in FIG. 10 taken along lines 12-12 is depicted in accordance with an illustrative embodiment. Although fastener system 1000 is depicted attaching first structure 316 to x-ray tube 310, some other type of fastener system may be used, depending on the implementation.

Figure 13:
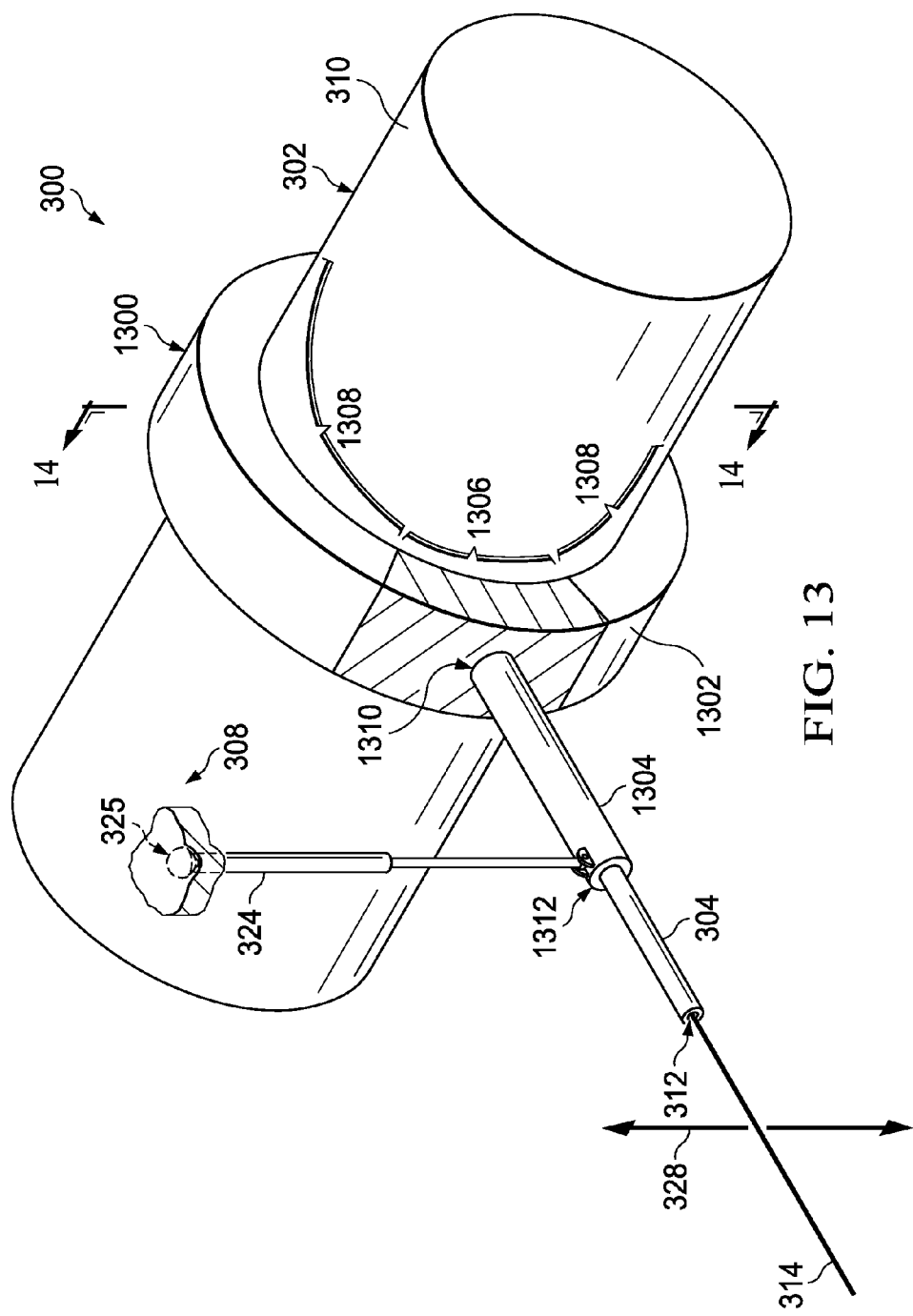
FIG. 13 is an illustration of a radiation generation system with a different bearing system in accordance with an illustrative embodiment.

With reference now to FIG. 13, an illustration of radiation generation system 300 from FIGS. 3-9 with a different bearing system is depicted in accordance with an illustrative embodiment. In this illustrative example, bearing system 1300 is used in radiation generation system 300 instead of bearing system 306 in FIGS. 3-9.

As depicted, bearing system 1300 comprises first structure 1302 and second structure 1304. First structure 1302 has a toroidal-type shape in this illustrative example. First structure 1302 is configured to wrap around x-ray tube 310. Portion 1306 of first structure 1302 is comprised of a shielding material, while portion 1308 of first structure 1302 is comprised of a material lighter than the shielding material. Further, second structure 1304 is also comprised of this shielding material.

Second structure 1304 has an elongate shape with first end 1310 and second end 1312. First end 1310 of second structure 1304 is connected to first structure 1302. This connection is a fixed connection. Second end 1312 of second structure 1304 is configured to receive and hold collimator 304.

With this configuration for bearing system 1300, movement system 308 only uses first actuator 324 to move bearing system 1300. Second actuator 326 from FIGS. 3-9 may be excluded. First actuator 324 may be configured to lengthen or shorten to move second structure 1304. Movement of second structure 1304 by first actuator 324 causes second structure 1304 with first structure 1302 to rotate around x-ray tube 310. First structure 1302 and second structure 1304 are only rotated within a selected range of degrees. Rotation of second structure 1304 causes a location on an object at which x-ray beam 314 is pointed to move in a direction along axis 328.

Figure 14:
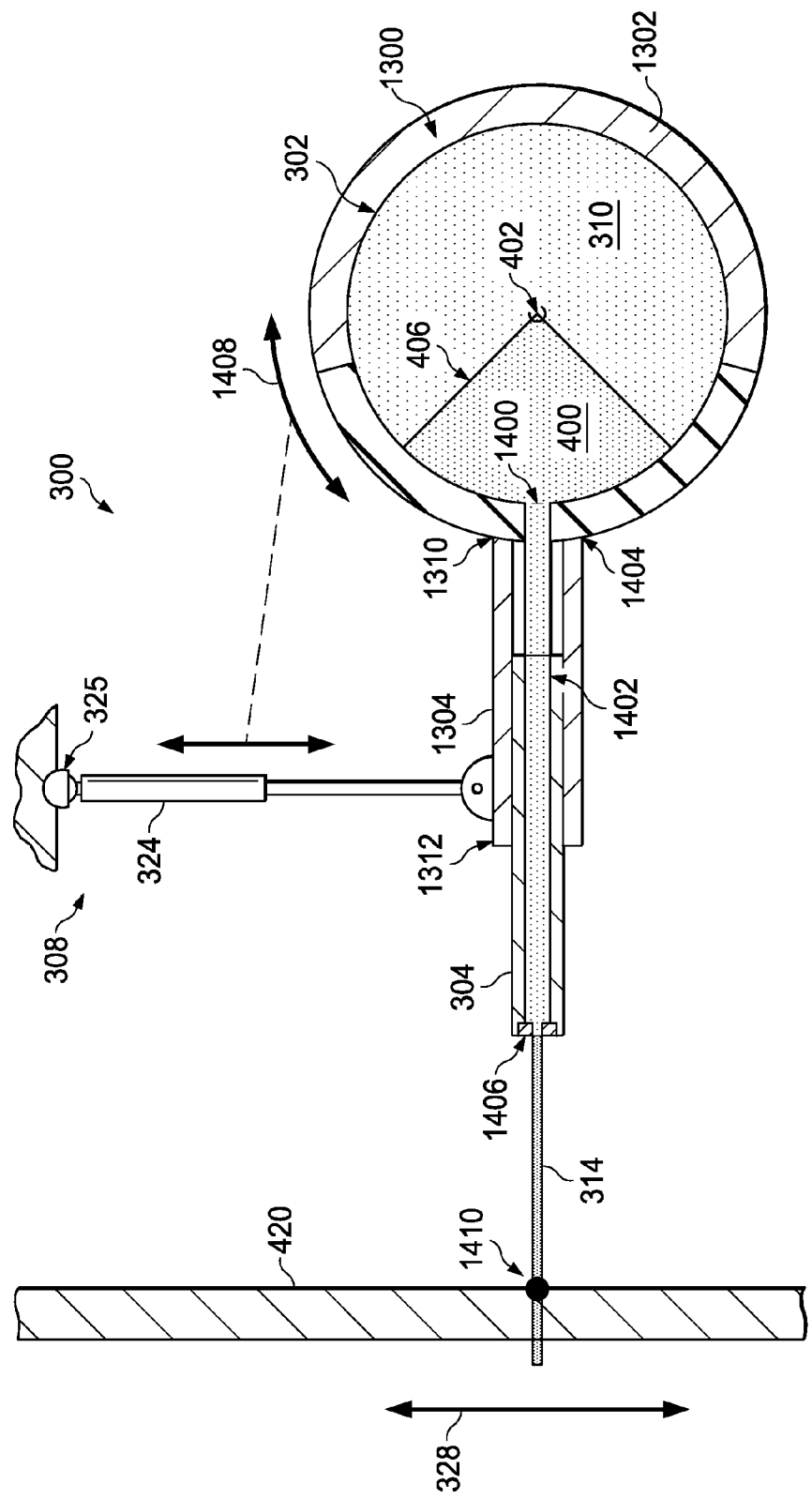
FIG. 14 is an illustration of a cross-sectional view of a radiation generation system in accordance with an illustrative embodiment.
Figure 15:
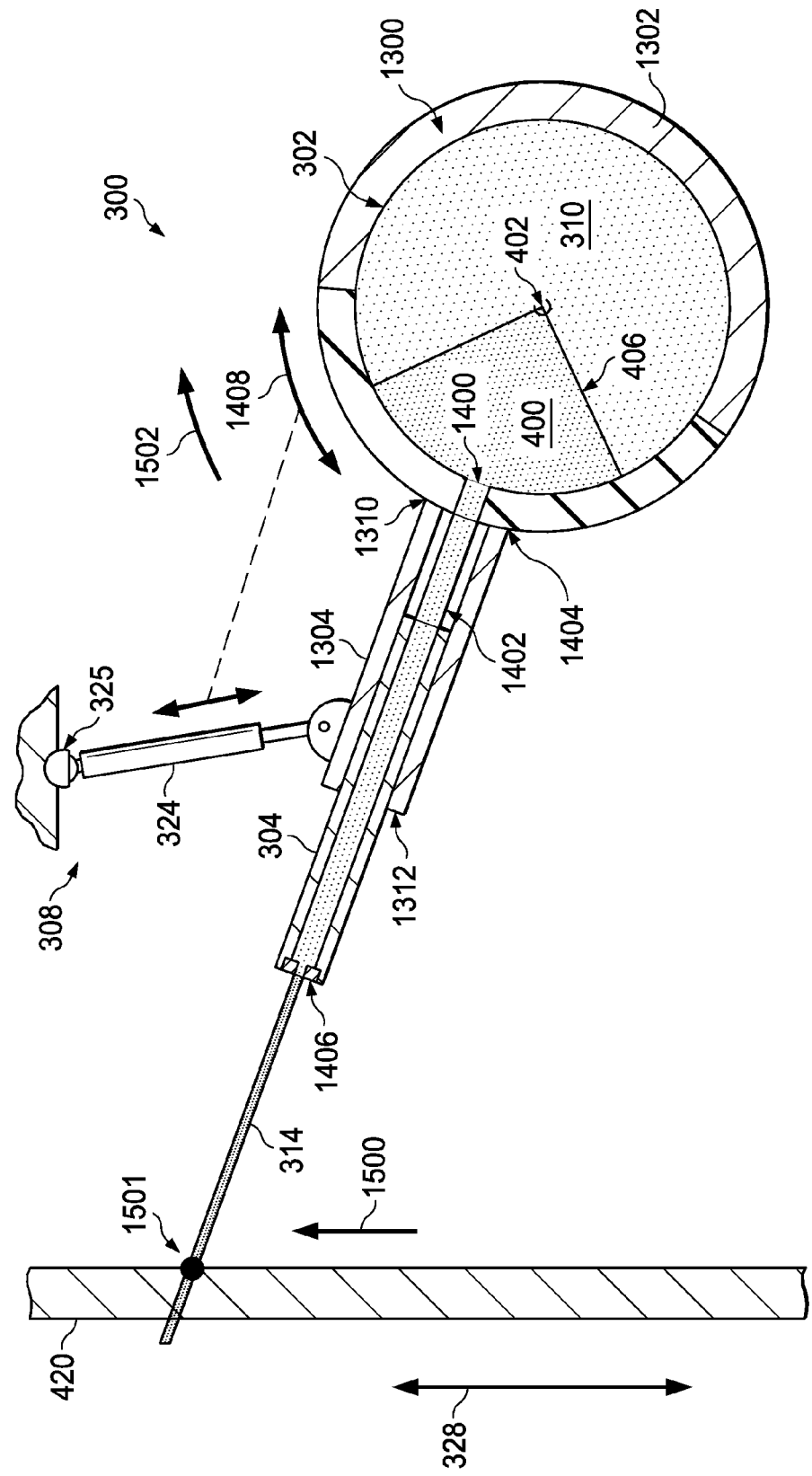
FIG. 15 is an illustration of a cross-sectional view of a radiation generation system in accordance with an illustrative embodiment.
Figure 16:
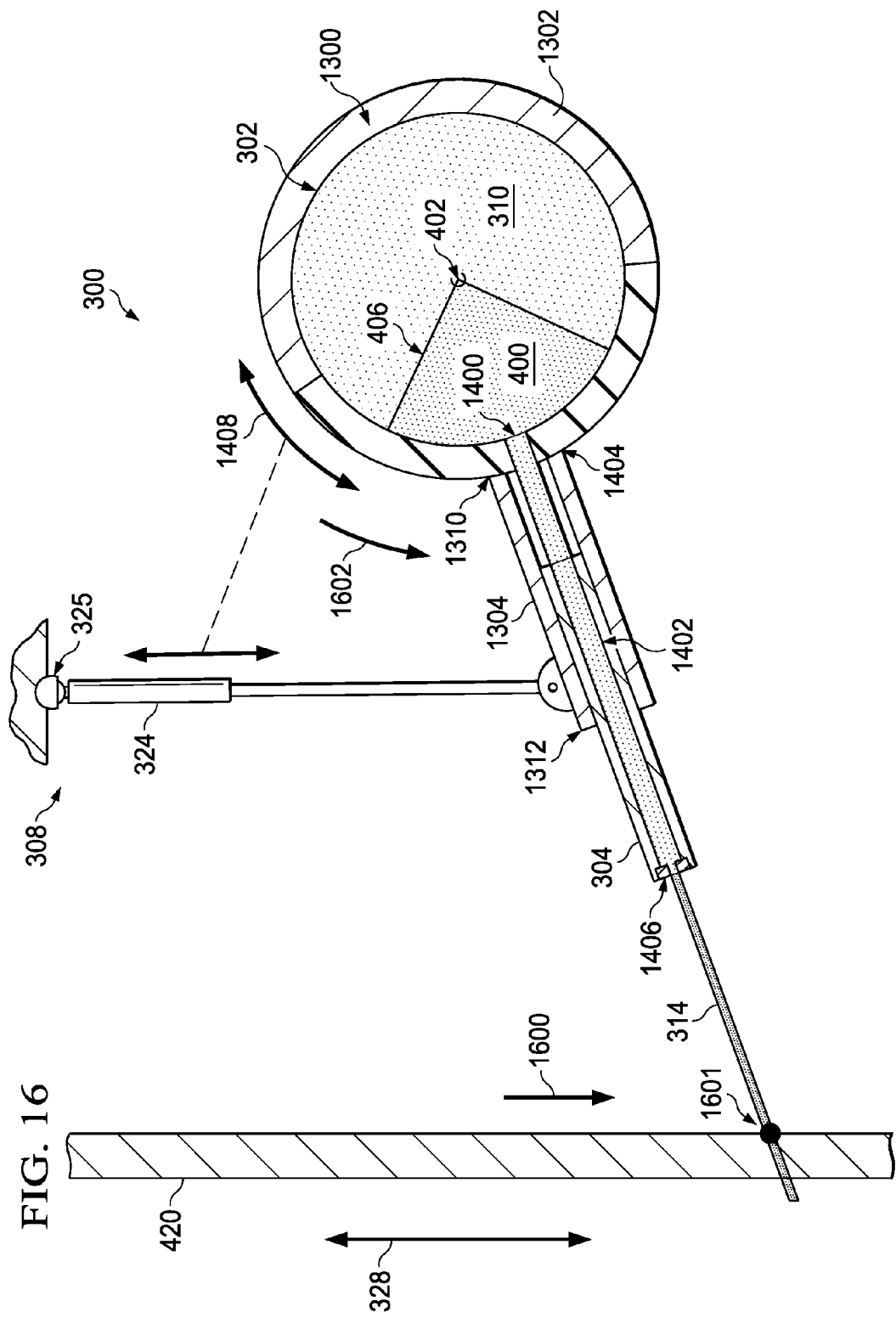
FIG. 16 is an illustration of a cross-sectional view of a radiation generation system in accordance with an illustrative embodiment.

With reference now to FIGS. 14-16, illustrations of a cross-sectional view of radiation generation system 300 in FIG. 13, taken along lines 14-14 in FIG. 13, are depicted in accordance with an illustrative embodiment. In FIG. 14, first structure 1302 has window 1400 that allows a portion of x-rays 400 to pass through first structure 1302. In this illustrative example, window 1400 takes the form of an open channel. As depicted, bearing system 1300 provides shielding for the portion of x-rays 400 generated by x-ray tube 310 that do not form x-ray beam 314.

Second structure 1304 has channel 1402 that extends through the entire length of second structure 1304 from first end 1404 of second structure 1304 to second end 1406 of second structure 1304. In this illustrative example, channel 1402 has the same size from first end 1404 to second end 1406. Second structure 1304 is configured to receive and hold collimator 304 at second end 1406.

As depicted, first actuator 324 may be lengthened or shortened to move second structure 1304. Movement of second structure 1304 may cause first structure 1302 with second structure 1304 to rotate in the direction of arrow 1408 about center point 402 around x-ray tube 310. In other words, first actuator 324 may be lengthened or shortened to rotate all of bearing system 1300 around x-ray tube 310 in the direction of arrow 1408. X-ray tube 310 remains stationary, while bearing system 1300 is rotated about center point 402. Rotation of bearing system 1300 causes location 1410 on object 420 at which x-ray beam 314 is pointed to move in a direction along axis 328.

Turning now to FIG. 15, movement system 308 has been operated such that location 1410 on object 420 at which x-ray beam 314 was pointed in FIG. 14 has been moved in the direction of arrow 1500 to location 1501. In particular, second structure 1304 has been rotated about center point 402 in the direction of arrow 1502 to change the direction in which x-ray beam 314 is pointing.

Turning now to FIG. 16, movement system 308 has been operated such that location 1410 on object 420 at which x-ray beam 314 was pointed in FIG. 14 has been moved in the direction of arrow 1600 to location 1601. In particular, second structure 1304 has been rotated about center point 402 in the direction of arrow 1602 to change the direction in which x-ray beam 314 is pointing.

The illustrations of radiation generation system 300 in FIGS. 3-16 are not meant to imply physical or architectural limitations to the manner in which different x-ray systems may be implemented in accordance with an illustrative embodiment. Other components in addition to or in place of the ones illustrated may be used. Some components may be optional.

The different components shown in FIGS. 3-16 may be combined with components in FIG. 2, used with components in FIG. 2, or a combination of the two. Additionally, some of the components in FIGS. 3-16 may be illustrative examples of how components shown in block form in FIG. 2 can be implemented as physical structures.

Figure 17:
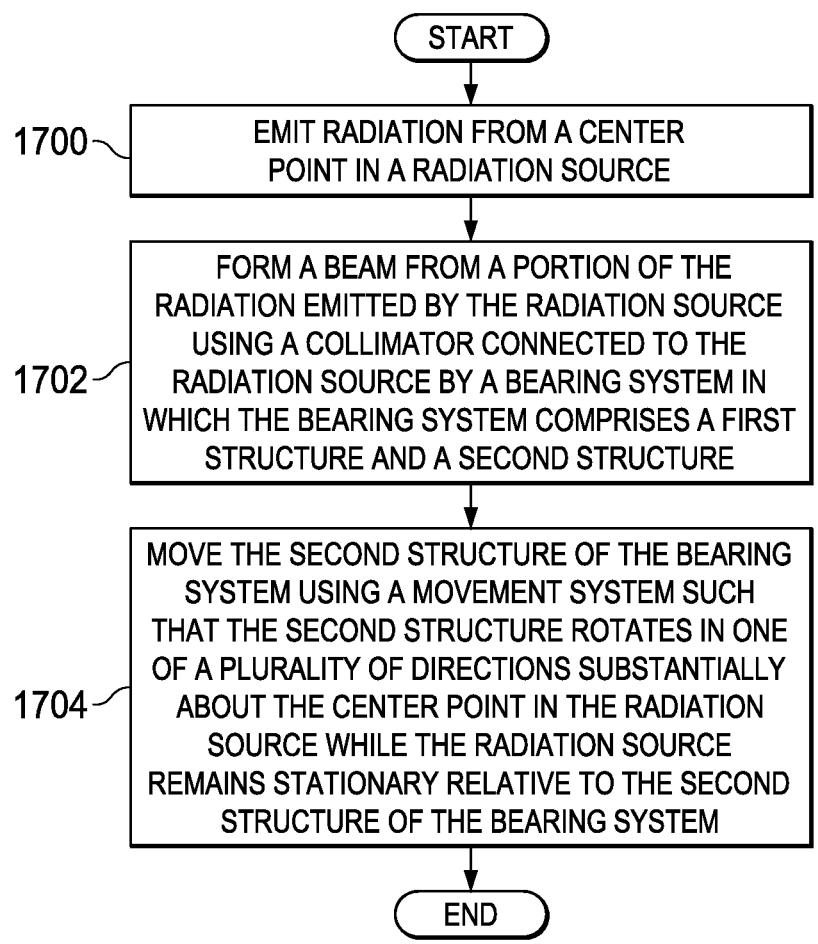
FIG. 17 is an illustration of a process for steering a beam emitted by a radiation generation system, in the form of a flowchart, in accordance with an illustrative embodiment.

Turning now to FIG. 17, an illustration of a process for steering a beam emitted by a radiation generation system in the form of a flowchart is depicted in accordance with an illustrative embodiment. The process illustrated in FIG. 17 may be implemented in inspection environment 200 in FIG. 2. In particular, the process may be implemented using radiation generation system 212 in backscatter inspection system 202 in FIG. 2.

The process begins by emitting radiation from a center point in a radiation source (operation 1700). Thereafter, a beam is formed from a portion of the radiation emitted by the radiation source using a collimator connected to the radiation source by a bearing system in which the bearing system comprises a first structure and a second structure (operation 1702).

The first structure of the bearing system is associated with the radiation source and the second structure of the bearing system is connected to the first structure. The second structure is also configured to hold the collimator.

A movement system is used to move the second structure of the bearing system such that the second structure rotates in one of a plurality of directions substantially about the center point in the radiation source while the radiation source remains stationary relative to the second structure of the bearing system (operation 1704), with the process terminating thereafter. Rotation of the second structure substantially about the center point in the radiation source changes a direction in which the beam formed by the collimator is directed. The movement system, the bearing system, the collimator, and the radiation source form a radiation generation system for a backscatter inspection system.

If the connection between the second structure and the first structure in the bearing system is a fixed connection, movement of the second structure by the movement system also causes rotation of the first structure substantially about the center point in the radiation source. If the second structure is moveably connected to the first structure, the first structure remains stationary relative to the second structure when the second structure rotates substantially about the center point in the radiation source. Operation 1704 may be performed any number of times while inspecting an object to move the beam along an object in a selected pattern.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 18:
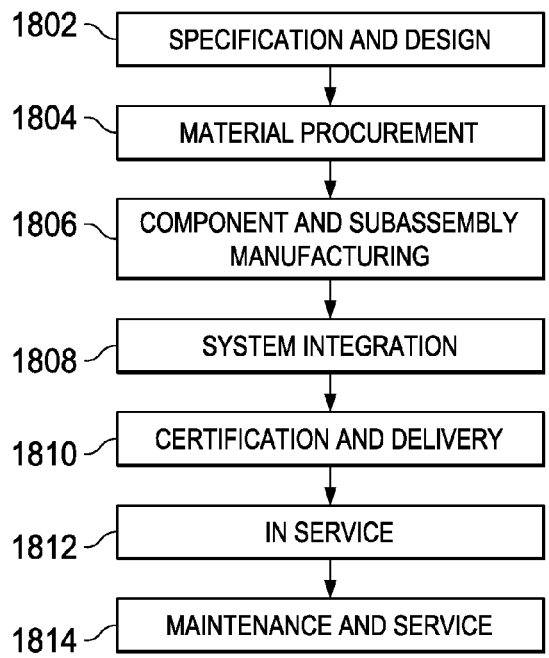
FIG. 18 is an illustration of an aircraft manufacturing and service method in accordance with an illustrative embodiment.
Figure 19:
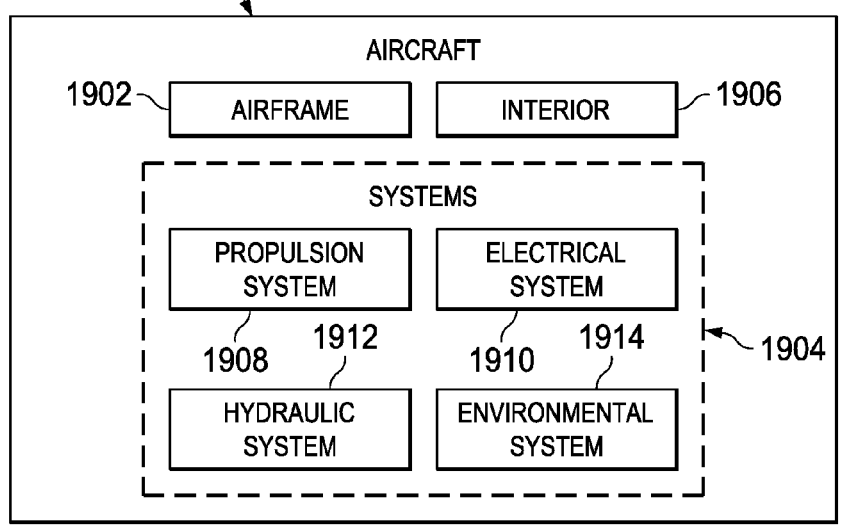
FIG. 19 is an illustration of an aircraft in which an illustrative embodiment may be implemented.

Illustrative embodiments of the disclosure may be described in the context of aircraft manufacturing and service method 1800 as shown in FIG. 18 and aircraft 1900 as shown in FIG. 19. Turning first to FIG. 18, an illustration of an aircraft manufacturing and service method is depicted in accordance with an illustrative embodiment. During pre-production, aircraft manufacturing and service method 1800 may include specification and design 1802 of aircraft 1900 in FIG. 19 and material procurement 1804.

During production, component and subassembly manufacturing 1806 and system integration 1808 of aircraft 1900 in FIG. 19 takes place. Thereafter, aircraft 1900 in FIG. 19 may go through certification and delivery 1810 in order to be placed in service 1812. While in service 1812 by a customer, aircraft 1900 in FIG. 19 is scheduled for routine maintenance and service 1814, which may include modification, reconfiguration, refurbishment, and other maintenance or service.

Each of the processes of aircraft manufacturing and service method 1800 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 19, an illustration of an aircraft is depicted in which an illustrative embodiment may be implemented. In this example, aircraft 1900 is produced by aircraft manufacturing and service method 1800 in FIG. 18 and may include airframe 1902 with plurality of systems 1904 and interior 1906. Examples of systems 1904 include one or more of propulsion system 1908, electrical system 1910, hydraulic system 1912, and environmental system 1914. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1800 in FIG. 18. For example, backscatter inspection system 202 in FIG. 2 may be used to inspect aircraft 1900, a portion of aircraft 1900, or a particular part for aircraft 1900 during component and subassembly manufacturing 1806, system integration 1808, certification and delivery 1810, in service 1812, and/or maintenance and service 1814.

In one illustrative example, components or subassemblies produced in component and subassembly manufacturing 1806 in FIG. 18 may be fabricated or manufactured in a manner similar to components or subassemblies produced while aircraft 1900 is in service 1812 in FIG. 18. As yet another example, one or more apparatus embodiments, method embodiments, or a combination thereof may be utilized during production stages, such as component and subassembly manufacturing 1806 and system integration 1808 in FIG. 18. One or more apparatus embodiments, method embodiments, or a combination thereof may be utilized while aircraft 1900 is in service 1812 and/or during maintenance and service 1814 in FIG. 18. The use of a number of the different illustrative embodiments may substantially expedite the assembly of and/or reduce the cost of aircraft 1900.

Thus, one or more illustrative embodiments may be used to inspect objects in which an inconsistency may be present. With the configuration for a radiation generation system described in the different illustrative embodiments, a backscatter inspection system may be made smaller and lighter and may fit more easily into enclosed spaces as compared to currently used backscatter inspection systems. Thus, inspections of objects, such as aircraft, may be made with less disassembly, time, and cost.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a radiation source configured to emit radiation selected from the group consisting of: X-rays, gamma rays, and neutrons;
a collimator configured to form a beam using a portion of the radiation emitted by the radiation source;
a bearing system connecting the collimator to the radiation source, wherein the bearing system comprises:
a first structure connected to the radiation source; and
a second structure connected to the first structure at a connection, the second structure holding the collimator; and
a movement system configured to move the second structure of the bearing system such that the second structure rotates in one of a plurality of directions substantially about a center point in the radiation source while the radiation source remains stationary relative to the second structure, wherein rotation of the second structure substantially about the center point changes a direction in which the beam formed by the collimator is directed, wherein the connection between the first structure and the second structure is a fixed connection, and wherein movement of the second structure causes the second structure and the first structure to rotate in the one of the plurality of directions substantially about the center point around the radiation source within a selected range of degrees.

2. The apparatus of claim 1, wherein the first structure has a window configured to allow at least a portion of the radiation emitted from the center point of the radiation source to pass through the first structure.

3. The apparatus of claim 1, wherein the second structure has a channel that extends from a first end of the second structure to a second end of the second structure.

4. The apparatus of claim 3, wherein a size of the channel in the second structure changes along a length of the second structure.

5. The apparatus of claim 3, wherein a portion of the channel at the second end of the second structure receives and holds the collimator.

6. The apparatus of claim 1, wherein a first end of the second structure has a concave spherical shape substantially conforming to a curved shape of the first structure and wherein a second end of the second structure has an elongate shape.

7. The apparatus of claim 1, wherein the radiation source is an x-ray tube and the radiation emitted from the x-ray tube is the x-rays.

8. The apparatus of claim 1, wherein at least a portion of the first structure and at least a portion of the second structure comprises a shielding material in which the shielding material covers a portion of the radiation source.

9. The apparatus of claim 1, wherein the first structure has a toroidal-type shape.

10. The apparatus of claim 1, wherein the bearing system is configured to move independently of the radiation source such that the radiation source remains stationary relative to the bearing system when the second structure rotates substantially about the center point.

11. The apparatus of claim 1 further comprising:
a detector system configured to detect backscatter formed in response to the beam encountering an object and generate data in response to detecting the backscatter.

12. The apparatus of claim 11, further comprising:
a computer system in communication with the detector system, wherein the computer system is configured to receive the data and generate a number of images of the object using the data in which the number of images is used to detect an inconsistency in the object.

13. The apparatus of claim 1, wherein the apparatus further comprises a backscatter detector controlled by the computer to detect backscatter, wherein the radiation source, the collimator, the bearing system, the backscatter detector, and the movement system form a radiation generation system in a backscatter inspection system, wherein the backscatter inspection system further comprises:
a back scatter image generator that generates an image from the detected backscatter; and
a moveable platform, wherein the radiation generation system is connected to the moveable platform.

14. A method for inspecting an object by an apparatus under computer control that performs method steps, the apparatus comprising a control computer, a radiation source, a collimator, a movement system, and a detector, the method comprising:
emitting radiation from a radiation source under control of the control computer, the radiation selected from the group consisting of: X-rays, gamma rays, and neutrons;
forming a beam from a portion of the radiation emitted by the radiation source using a collimator, wherein the collimator is connected to the radiation source by a bearing system comprising a first structure associated with the radiation source and a second structure connected to the first structure in which the second structure holds the collimator;
moving the second structure of the bearing system using the movement system, under control of the control computer, such that the second structure rotates in one of a plurality of directions substantially about a center point in the radiation source while the radiation source remains stationary relative to the second structure, wherein rotation of the second structure substantially about the center point in the radiation source changes a direction in which the beam formed by the collimator is directed, wherein a connection between the first structure and the second structure is a fixed connection and wherein movement of the second structure causes the second structure and the first structure to rotate in the one of the plurality of directions substantially about the center point around the radiation source within a selected range of degrees;
directing, using the movement system, the beam toward the object;
detecting, using the detector under control of the control computer, backscatter formed in response to the beam encountering the object; and
generating an image of the object from the detected backscatter.

* * * * *